United States Patent
Yamada et al.

(10) Patent No.: US 9,804,470 B2
(45) Date of Patent: Oct. 31, 2017

(54) ORGANIC COMPOUND AND ELECTROCHROMIC ELEMENT CONTAINING THE SAME

(71) Applicant: CANON KABUSHIKI KAISHA, Tokyo (JP)

(72) Inventors: Kenji Yamada, Yokohama (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 742 days.

(21) Appl. No.: 14/046,553

(22) Filed: Oct. 4, 2013

(65) Prior Publication Data
US 2014/0098282 A1 Apr. 10, 2014

(30) Foreign Application Priority Data
Oct. 5, 2012 (JP) ................ 2012-222899

(51) Int. Cl.
G02F 1/15 (2006.01)
G02F 1/157 (2006.01)
C07D 333/16 (2006.01)
C09K 9/02 (2006.01)

(52) U.S. Cl.
CPC ......... G02F 1/1521 (2013.01); C07D 333/16 (2013.01); C09K 9/02 (2013.01); G02F 1/157 (2013.01)

(58) Field of Classification Search
USPC ............... 348/342; 549/59; 359/265–275; 252/500
See application file for complete search history.

(56) References Cited

FOREIGN PATENT DOCUMENTS

| EP | 2719702 | * | 4/2014 |
| JP | 56-67881 A | | 6/1981 |

OTHER PUBLICATIONS

Graf et al. Organometallic Terthiophene Derivatives: Modulation of the Terthiophene Core of 5,5"-Diphenyl-2,2':5'2"-Tertthiophene via [CpRu]+ and [Cp*Ru]+ substituent; Inorg. Chem. 1997, 36, 141-149.*

Zgou et al., Structural and Electronic properties of New materials based on thiophene and phenylene, Acta Phys.-Chim, Sin., 2008, 24(1): 37-40.*

David D.Graf and Kent R.Mann, "Organometallic Terthiophene Derivatives . . . ", Inorganic Chemistry 1997,36,141-149.

* cited by examiner

*Primary Examiner* — Monique Peets
(74) *Attorney, Agent, or Firm* — Canon U.S.A., Inc. IP Division

(57) ABSTRACT

An organic compound having the following general formula [1]:

[Chem. 1]

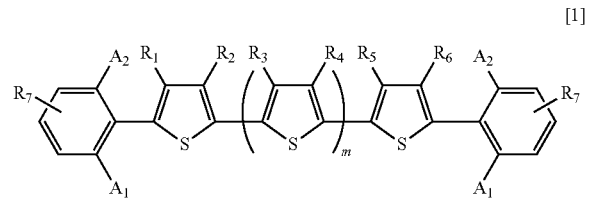

wherein A1 and A2 independently denote a hydrogen atom or a substituent,

R7 denotes a hydrogen atom or a substituent,

R2 to R5 denote a substituent,

R1 and R6 independently denote a hydrogen atom or a substituent, and m is 2 or 3.

10 Claims, 2 Drawing Sheets

ORGANIC COMPOUND AND ELECTROCHROMIC ELEMENT CONTAINING THE SAME

BACKGROUND OF THE INVENTION

Field of the Invention

The present invention relates to a novel electrochromic organic compound and an electrochromic element containing the organic compound.

Description of the Related Art

Various electrochromic (hereinafter also referred to as "EC") materials have been reported. The optical absorption characteristics (coloration or light transmittance) of electrochromic materials change through an electrochemical oxidation-reduction reaction. Metal oxides, such as $WO_3$, are known as inorganic EC materials. However, films of metal oxides are principally formed by vapor deposition, and it is difficult to form large metal oxide films.

Examples of known organic EC materials include electrically conductive polymers described in Japanese Patent Laid-Open No. 56-67881 and organic low molecular compounds, such as oligothiophenes described in David D. Graf and Kent R. Mann, Inorganic Chemistry, 1997, 36, 141. An electrically conductive polymer described in Japanese Patent Laid-Open No. 56-67881 can form an EC layer directly on an electrode by the electrolytic polymerization of a monomer.

Examples of known electrically conductive polymers that can form an EC layer include polythiophene, polyaniline, and polypyrrole. Electrochemical oxidation or reduction of these electrically conductive polymers results in changes in the π-conjugated chain length of the main chain, the electronic state of the highest occupied molecular orbital (HOMO), and the absorption wavelength.

These electrically conductive polymers have a long π-conjugated system and are colored in their neutral state because of absorption in the visible light region. The oxidation of the electrically conductive polymers shifts their absorption wavelengths toward the long wavelength side (infrared region side). A shift toward the infrared region side results in no absorption in the visible light region, and the EC element loses color.

An EC material of an oligothiophene compound described in David D. Graf and Kent R. Mann, Inorganic Chemistry, 1997, 36, 141 has a shorter π-conjugated chain length than electrically conductive polymers.

Thus, oligothiophene EC compounds in their neutral state often have an absorption peak in the ultraviolet region and look transparent to the human eye. An oxidation reaction converts an oligothiophene to a radical cation, which has absorption in the visible light region and is colored.

Organic EC materials are sometimes not transparent even in their colorless state. No organic EC material is known to have both high transparency in its colorless state and absorption in a visible long wavelength region in its colored state. Organic EC materials are often unstable under repeated oxidation and reduction.

An electrically conductive polymer described in Japanese Patent Laid-Open No. 56-67881 in its neutral state has an absorption band in the visible light region. Thus, a portion subjected to an insufficient electrochemical reaction remains colored even in its oxidized state and rarely has high transparency.

The stability of electrically conductive polymers is increased through intramolecular delocalization of a generally unstable radical cation. Nevertheless, because of their insufficient stability, electrically conductive polymers may deteriorate during repetitive oxidation-reduction reactions and consequently have poor performance.

Organic low-molecular oligothiophene EC compounds in their neutral state often have absorption in the ultraviolet region. With an increase in the number of thiophene rings constituting an oligothiophene EC compound and the conjugation length, the absorption edge of the oligothiophene EC compound extends to the visible range, and transparency in the colorless state decreases.

In fact, in an EC compound based on a thiophene trimer derivative described in David D. Graf and Kent R. Mann, Inorganic Chemistry, 1997, 36, 141, a structure composed of three thiophene rings has a relatively long conjugation length.

Thus, while the absorption peak in an oxidized colored state is approximately 660 nm in the visible long wavelength region, the absorption edge in the neutral state extends to approximately 500 nm. Thus, the EC compound has visible absorption and insufficient transparency even in its colorless state.

When the number of thiophene rings is decreased to shorten the conjugation length in order to improve transparency in the neutral colorless state, it is known that the visible absorption wavelength in the oxidized colored state is also an absorption band in the range of approximately 400 to 600 nm.

Thus, it is difficult to achieve both high transparency in the colorless state and absorption in a long wavelength region, particularly absorption in a long wavelength range of 600 nm or more, in the colored state.

Furthermore, because of a shorter conjugation length of an oligothiophene compound than electrically conductive polymers, there is also a problem in radical cation stability in the oxidized state.

SUMMARY OF THE INVENTION

In view of such situations, the present invention provides an electrochromic organic compound that has both high transparency with no optical absorption in the visible light region in its colorless state and absorption in a long wavelength region in its colored state and is stable under repeated oxidation and reduction.

The present invention provides an organic compound having the following general formula [1]:

[Chem. 1]

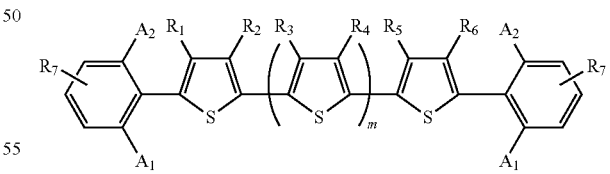

wherein A1 and A2 independently denote a hydrogen atom, an alkyl group containing 1 or more and 20 or less carbon atoms, an alkoxy group containing 1 or more and 20 or less carbon atoms, or an optionally substituted aryl group.

At least one of A1 and A2 denotes the alkyl group, the alkoxy group, or the aryl group.

The aryl groups denoted by A1 and A2 may have an alkyl group containing 1 or more and 8 or less carbon atoms or an alkoxy group containing 1 or more and 8 or less carbon atoms as a substituent.

R7 denotes a hydrogen atom, a halogen atom, an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group.

The aryl group denoted by R7 may have an alkyl group containing 1 or more and 4 or less carbon atoms as a substituent.

R2, R3, R4, and R5 independently denote an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group.

R1 and R6 independently denote a hydrogen atom, a halogen atom, an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group.

m is 2 or 3. R3's and R4's in the repeating unit may be the same or different.

Further features of the present invention will become apparent from the following description of exemplary embodiments with reference to the attached drawings.

DESCRIPTION OF THE EMBODIMENTS

Figure 1:
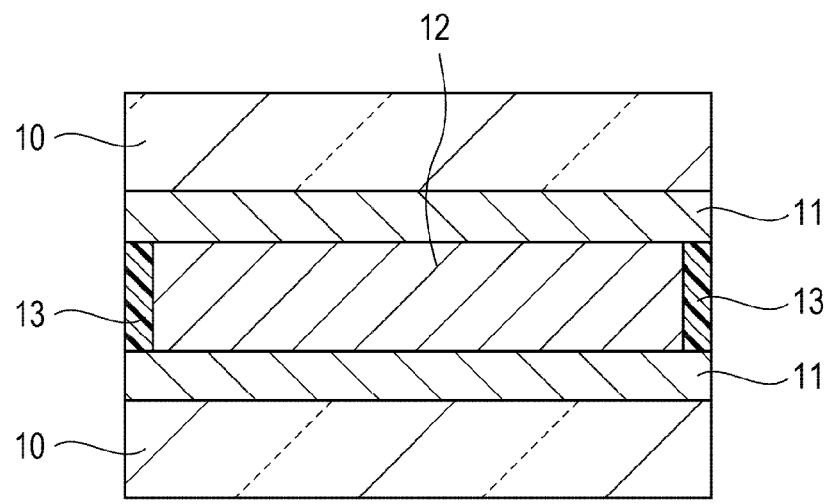
FIG. 1 is a schematic cross-sectional view of an electrochromic element according to an embodiment of the present invention.

An organic compound according to one embodiment of the present invention has the following general formula [1]:

As illustrated in the structure of the following general formula [1], an organic compound according to an embodiment of the present invention includes a structure (core portion) having a thiophene core skeleton, which serves as an optical absorption site, and a structure (cage portion) in which a phenyl group having an ortho substituent is introduced into the core skeleton.

A1 or A2 in the present embodiment denotes A1 or A2 in the general formula [1].

[Chem. 2]

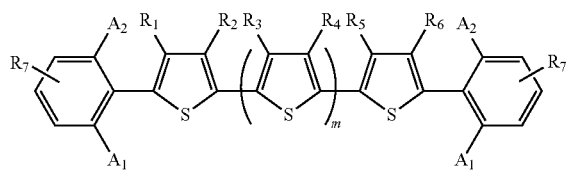

[1]

The skeleton of the core portion will be described below. The core portion in the general formula [1] has a thiophene skeleton. In the general formula [1], R2 to R5 independently denote an alkyl group containing 1 or more and 20 or less carbon atoms, an alkoxy group containing 1 or more and 20 or less carbon atoms, an optionally substituted aryl group, an alkyl ester group containing 1 or more and 20 or less carbon atoms, an optionally substituted amino group, or a cyano group.

The aryl group may have an alkyl group containing 1 or more and 8 or less carbon atoms or an alkoxy group containing 1 or more and 8 or less carbon atoms as a substituent.

The alkyl groups containing 1 or more and 20 or less carbon atoms denoted by R2 to R5 may be linear, branched, or cyclic. Specific examples of the alkyl group include a methyl group, an ethyl group, a n-propyl group, an isopropyl group, a n-butyl group, a tert-butyl group, a pentyl group, a hexyl group, an octyl group, a dodecyl group, a cyclohexyl group, a bicyclooctyl group, and an adamantyl group. A hydrogen atom of the alkyl group may be substituted by a fluorine atom. For example, the alkyl group may be a trifluoromethyl group.

The alkyl group may be a methyl group, an ethyl group, a n-butyl group, or a hexyl group. The alkyl group may be a methyl group or an ethyl group.

The alkoxy groups denoted by R2 to R5 may be a methoxy group, an ethoxy group, an isopropoxy group, a n-butoxy group, a tert-butoxy group, an ethylhexyloxy group, an octyloxy group, or an ethylenedioxy group.

The aryl groups denoted by R2 to R5 may be a phenyl group, a biphenyl group, a fluorenyl group, a naphthyl group, a fluoranthenyl group, an anthryl group, a phenanthryl group, a pyrenyl group, or a perylenyl group. The aryl group containing a heteroatom may be a pyridyl group or an indolyl group. The aryl group may be a phenyl group or a pyridyl group.

The substituent of the aryl group may be a halogen atom, an alkyl group containing 1 or more and 4 or less carbon atoms, an alkoxy group containing 1 or more and 4 or less carbon atoms, an aryl group, an aralkyl group, a substituted amino group, or a substituted silyl group.

The alkyl ester groups containing 1 or more and 20 or less carbon atoms denoted by R2 to R5 may be a methyl ester group, an ethyl ester group, a n-propyl ester group, an isopropyl ester group, n-butyl ester group, a tert-butyl ester group, a tert-amyl ester group, a hexyl ester group, a heptyl ester group, an octyl ester group, an ethylhexyl ester group, a cyclopentyl ester group, or a cyclohexyl ester group.

The substituents denoted by R2 to R5 may be a substituted amino group, such as a dimethylamino group or a diphenylamino group, or a cyano group.

Examples of the substituents denoted by R1 and R6 are the same as the specific examples of the substituents denoted by R2 to R5, that is, alkyl groups, alkoxy groups, aryl groups, and alkyl ester groups. The substituents denoted by R1 and R6 may also be a hydrogen atom.

m is 2 or 3. A plurality of R3's and R4's may be the same or different.

The structure of the phenyl group constituting the cage portion will be described below. The phenyl group has an ortho substituent.

In the general formula [1], A1 and A2 independently denote a hydrogen atom, an alkyl group containing 1 or more and 20 or less carbon atoms, an alkoxy group containing 1 or more and 20 or less carbon atoms, or an optionally substituted aryl group.

At least one of A1 and A2 denotes the alkyl group, the alkoxy group, or the aryl group. The aryl group may have an alkyl group containing 1 or more and 4 or less carbon atoms or an alkoxy group containing 1 or more and 4 or less carbon atoms as a substituent.

Specific examples of the substituent denoted by A1 and A2 are the same as the specific examples of the substituent denoted by R2 to R5, that is, alkyl groups, alkoxy groups, aryl groups, and alkyl ester groups.

R7 denotes a hydrogen atom, a halogen atom, an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group. The aryl group may have an alkyl group containing 1 or more and 4 or less carbon atoms as a substituent.

Specific examples of the substituent denoted by R7 are the same as the specific examples of the substituents denoted by R2 to R5, that is, alkyl groups, alkoxy groups, aryl groups, and alkyl ester groups.

Among these substituents, electron-donating substituents are effective in increasing the electron density of the thiophene core.

Electron donation from a substituent decreases the oxidation potential and is effective in decreasing the driving voltage of an EC element and stabilizing a radical cation generated by oxidation.

Thus, the substituent denoted by R7 may be a methyl group, an ethyl group, a methoxy group, an isopropoxy group, or a dimethylamino group. These substituents have high electron-donating ability.

Among the substituents denoted by R7, polar substituents, such as alkoxy groups and alkyl ester groups, can increase solubility in polar solvents and are suitably used in EC elements in which their electrochromic layers and electrolyte layers are solution layers.

This is because such an EC material can be dissolved in an EC layer and an electrolyte layer at a high concentration to increase the contrast of the EC element in the colored state. From this standpoint, the substituent denoted by R7 may be a methyl ester group, an isopropyl ester group, a tert-butyl ester group, a methoxy group, or an isopropoxy group.

Figure 2:
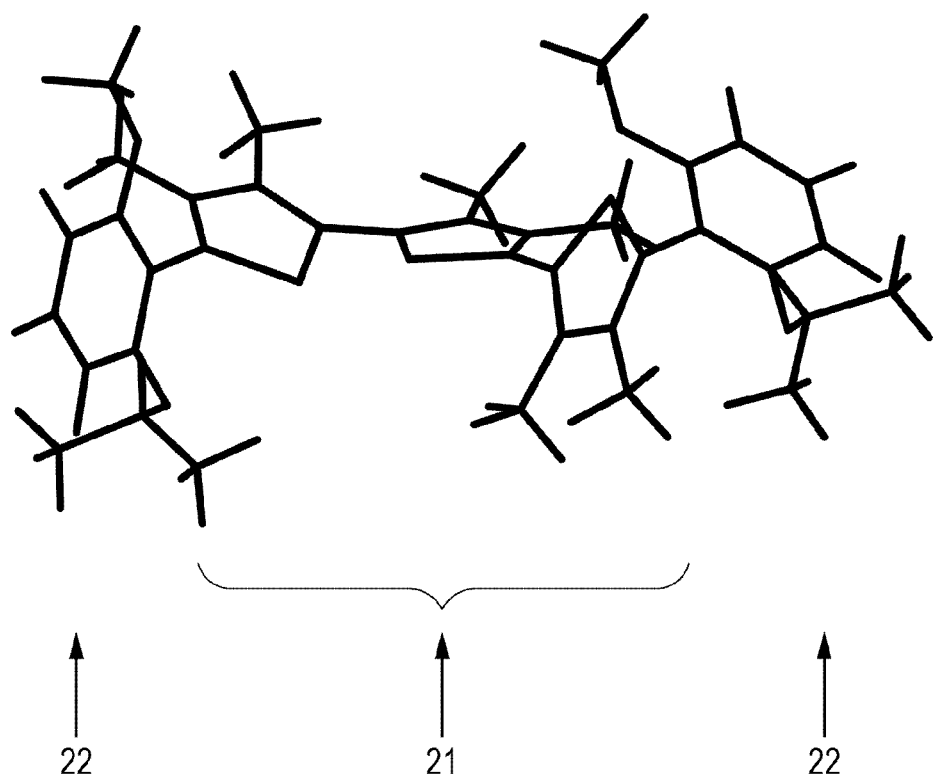
FIG. 2 is a molecule model of an organic compound according to an embodiment of the present invention.

FIG. 2 is a molecule model of an organic compound according to an embodiment of the present invention. The compound illustrated in FIG. 2 has the following chemical structure. The compound is an exemplary compound A-1 described below.

[Chem. 3]

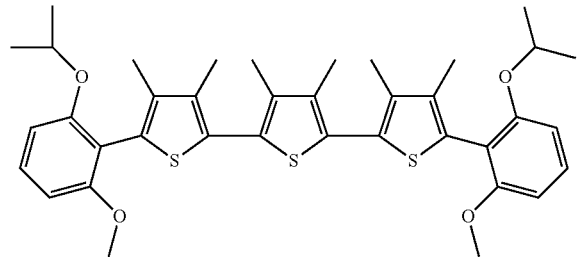

FIG. 2 illustrates a three-dimensional molecular structure in which A1 or A2 of an organic compound according to an embodiment of the present invention is an isopropoxy group or a methoxy group, R1 to R6 are methyl groups, and four successive 3,4-dimethylthiophenes constitute a core portion.

The three-dimensional structure illustrated in FIG. 2 was determined by structural optimization calculation in the ground state using a commercially available electronic state calculation software, Gaussian 03* Revision D.01.

The density functional theory was employed as quantum chemical calculation. B3LYP was used as a functional. In the Gaussian 03, Revision D.01, the basis function was 6-31G*.

* Gaussian 03, Revision D.01,

M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004.

In FIG. 2, 21 denotes a structure containing four successive 3,4-dimethylthiophene rings, and 22 denotes the cage portion containing a phenyl group having an isopropoxy group and a methoxy group.

In the 3,4-dimethylthiophene tetramer in the core portion 21, the thiophene rings have a twisted structure because of the steric hindrance of methyl groups at positions 3 and 4 of the thiophene rings.

Table 1 shows the dihedral angle between thiophene rings determined by molecular orbital calculation with respect to a compound A-1 according to an embodiment of the present invention and a compound having a core portion composed of an unsubstituted thiophene tetramer for comparison purposes.

The dihedral angle between thiophene rings of the compound A-1 is 61 degrees, indicating lower planarity than the unsubstituted compound, which has a dihedral angle of 24 degrees.

TABLE 1

| Compound | | |
|---|---|---|
| Dihedral angle between adjacent thiophene rings | 61 degrees | 24 degrees |

The thiophene skeleton structure serving as the core portion of an organic compound according to an embodiment of the present invention functions as an optical absorption site of the organic compound.

In the general formula [1], m is 2 or 3, and the total number of thiophene rings in the optical absorption site including thiophene rings adjacent to the cage portion is 4 or 5.

An oligothiophene contains a plurality of thiophene rings having a certain planarity and consequently has a long conjugated system. Thus, a thiophene tetramer or pentamer even in its neutral state absorbs light in the visible light region.

In the general formula [1] of a compound according to an embodiment of the present invention, the structures denoted by R2 to R5 are substituents having a large excluded volume, such as an alkyl group, and therefore these substituents cause steric hindrance between adjacent thiophene rings.

Thus, for the successive thiophene rings, a structure having a low planarity is favorable in terms of energy.

A low planarity results in a short π-conjugated system. This results in an increase in energy of absorbed light and a decrease in absorption wavelength.

Thus, an organic compound according to an embodiment of the present invention in its neutral state even having a core skeleton composed of a thiophene tetramer or pentamer absorbs light in the ultraviolet region. Because of no absorption in the visible light region, therefore, an organic compound according to an embodiment of the present invention has high transparency.

The organic compound in its oxidized state has a different electronic state from its neutral state and a higher molecular planarity than its neutral state and absorbs light in a long wavelength range, thereby assuming a colored state.

In contrast, electrically conductive polymers in their neutral state absorb light in the visible light region. Thus, even in their oxidized state, a portion subjected to an insufficient electrochemical reaction still has an absorption band in the visible light region (residual color).

On the other hand, an organic compound according to an embodiment of the present invention has no absorption band in the visible light region even in a portion subjected to an insufficient electrochemical reaction and can therefore maintain high transparency.

A radical cation derived from the oligothiophene core of a compound according to an embodiment of the present invention having a short π-conjugated system has lower stability than electrically conductive polymers.

Thus, a phenyl group having an ortho substituent is introduced into the thiophene core of an organic compound according to an embodiment of the present invention.

The steric hindrance of the ortho substituent of the phenyl group protects the radical cation derived from the core portion.

The instability of the radical cation results from recombination between the radicals or hydrogen abstraction in another molecule caused by radical cation due to high reactivity of the radical cation. In other words, the instability of the radical cation results from a radical reaction between the radical cation and another molecule.

Thus, the steric hindrance of the phenyl group having an ortho substituent bonded to the core portion can effectively increase the stability of the radical cation. This is because the steric hindrance group can prevent the radical cation from coming into contact with another molecule.

The structure of the phenyl group having the steric hindrance groups A1 and A2 (cage portion) protects the oxidation-coloring portion (core portion) from the attack of another electrochromic material molecule or another substrate that exists as an impurity. Thus, it is desirable that the phenyl group surround the core portion.

Thus, it is desirable that the phenyl group have a bulky substituent.

In order to increase the solubility of the compound in polar solvents, it is desirable that the steric hindrance groups A1 and A2 have polar substituents, such as an alkoxy group. Thus, the steric hindrance groups may be bulky groups, such as a methoxy group or a more bulky group.

It is desirable that the cage portion and the core portion have less electronic resonance. When the cage portion includes a π-electron system, such as an aromatic ring, the electronic resonance between the cage portion and the core portion can be decreased to reduce the extension of the highest occupied molecular orbital (HOMO) localized in the core portion to the cage portion.

Although the molecular orbital is not clearly defined in actual molecules because of fluctuation due to thermal motion or quantum-chemical fluctuation, orthogonal π electron orbitals of the cage portion and the core portion have little resonance. Thus, it is desirable that the phenyl group of the cage portion bonded to the core portion be orthogonal to the molecular plane of the core portion.

From this standpoint, the phenyl group having substituents at both of the ortho positions is preferred to phenyl groups having a substituent at one of the ortho positions.

From the standpoint of the cage effect, it is also desirable that the cage portion has higher oxidation potential than the core portion and be resistant to oxidation.

Since the radical cation is localized in the core portion during oxidation in such a structure, the shielding structure of the cage portion can protect the radical cation from the attack of another substance, thereby significantly improving the stability of the radical cation.

Furthermore, the electron density of the core portion can be increased to stabilize the radical cation in the core portion. Thus, it is desirable that the substituents A1 and A2 of the phenyl group in the cage portion be electron-donating substituents.

Examples of the substituents having high electron-donating ability and steric hindrance include an isopropoxy group, a tert-butoxy group, and an ethylhexyloxy group.

The following are specific structural formulae of a compound according to an embodiment of the present invention. A compound according to an embodiment of the present invention is not limited to these.

[Chem. 4]

A-1

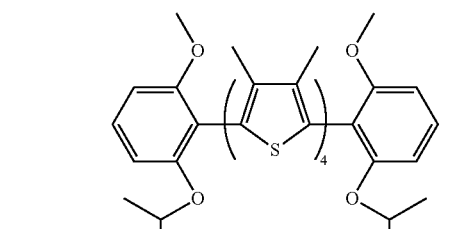

A-2

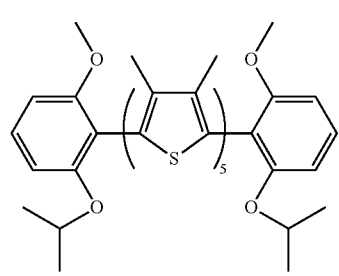

A-3

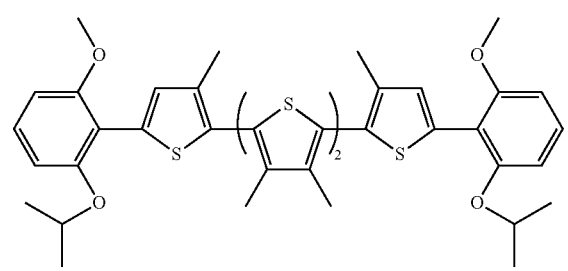

A-4

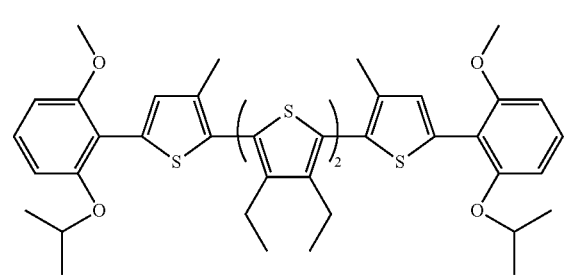

A-5

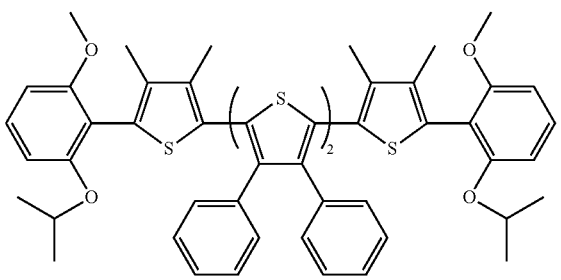

A-6

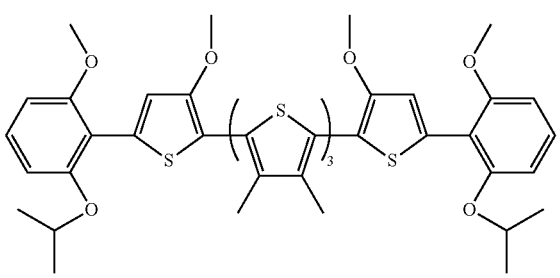

[Chem. 5]

A-7

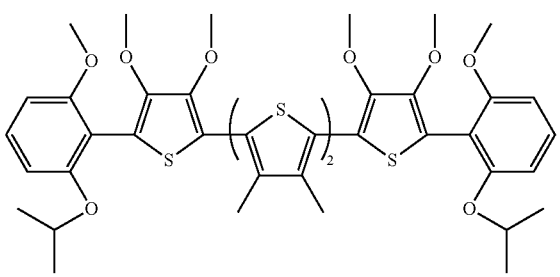

A-8

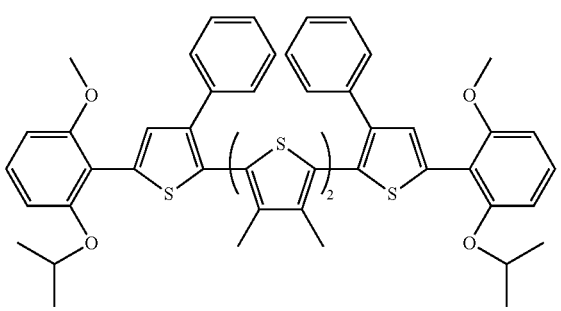

A-9

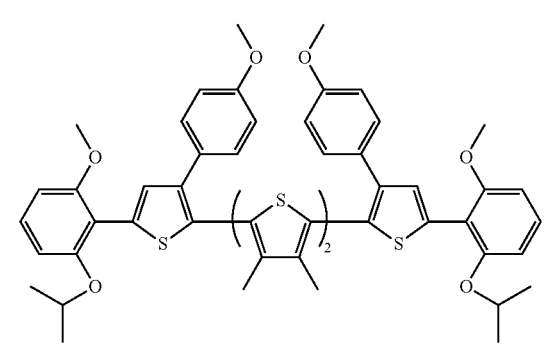

A-10
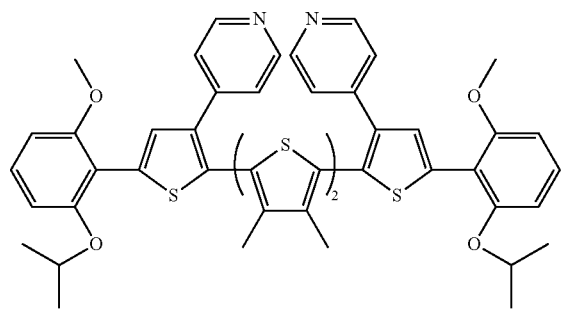
A-11
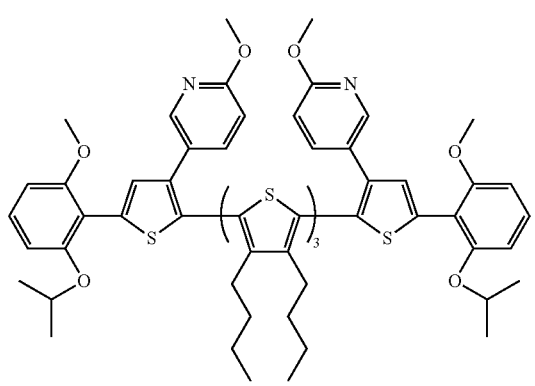
[Chem. 6]
A-12
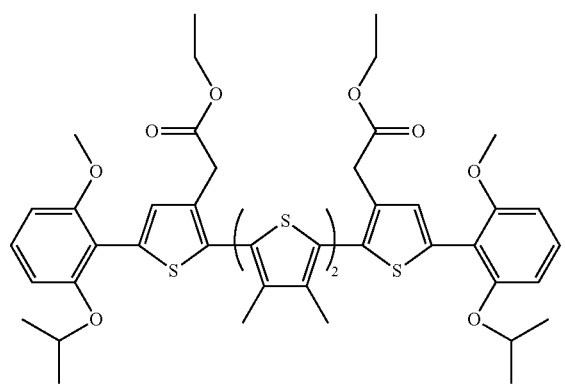
A-13
A-14
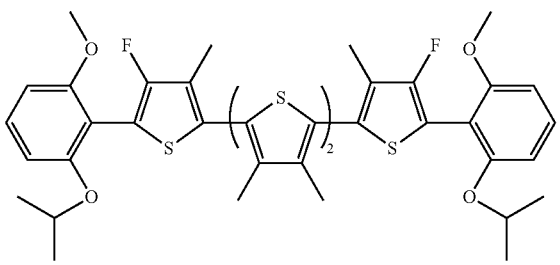
A-15
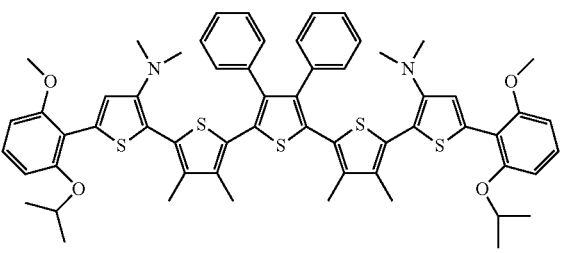
A-16
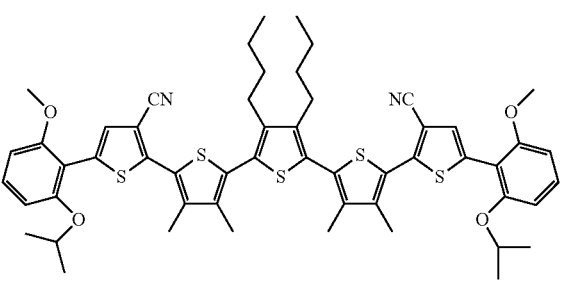
[Chem. 7]
B-1
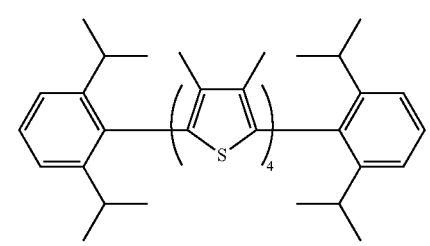
B-2
B-3
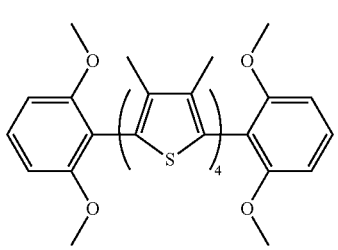

B-4 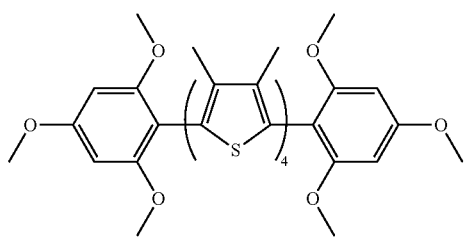

B-5 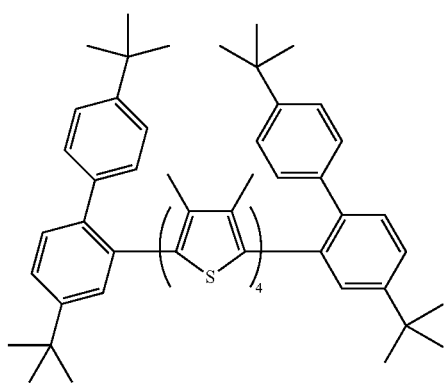

B-6 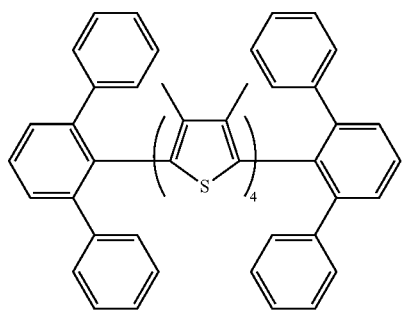

[Chem. 8]

B-7 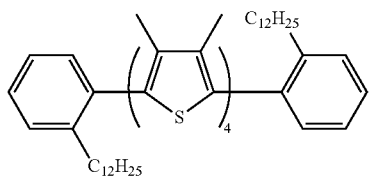

B-8 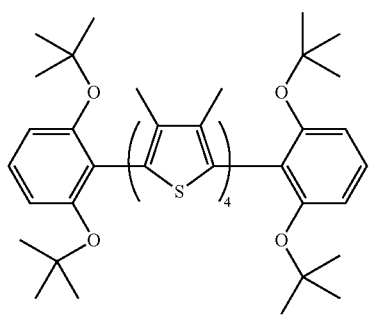

B-9 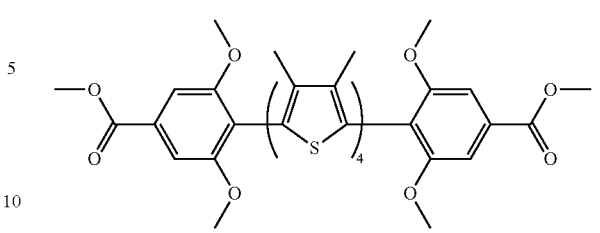

B-10 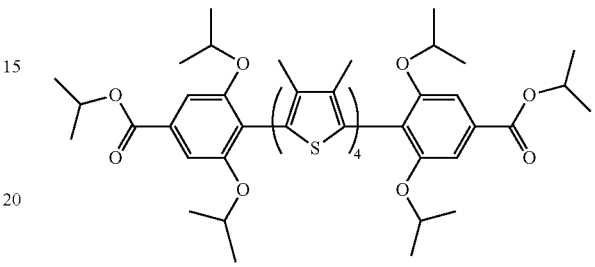

B-11 

B-12 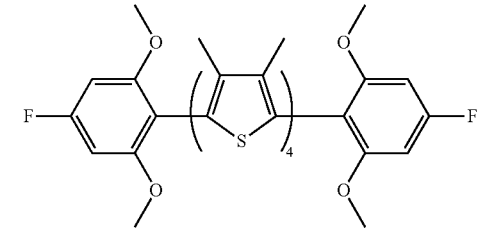

In the group A compounds, the substituents A1 and A2 of the cage portion in the general formula [1] are a methoxy group and an isopropoxy group, and the thiophene rings have the substituents R1 to R6 having various structures.

In the group B compounds, the core portion is a dimethylthiophene tetramer in which all the substituents R1 to R6 are methyl groups, and A1, A2, and R7 in the cage portion have various structures.

In these compounds, adjacent thiophene rings have low planarity because of the substituents R2 to R5.

The thiophene skeleton of the core portion is protected by steric hindrance due to the cage effect of A1 and A2 at the ortho positions of the substituted phenyl group.

Thus, these organic EC compounds have high transparency in their colorless state, absorption in a long wavelength region in the oxidized colored state, and high durability in repetitive oxidation-reduction reactions.

A compound according to an embodiment of the present invention can be synthesized in accordance with the following reaction scheme.

In the scheme, X denotes a halogen atom. A compound according to an embodiment of the present invention can be synthesized by a coupling reaction between a thiophene halogenide and a boronic acid or boronic acid ester compound of a phenyl group having an ortho substituent or between a boronic acid or boronic acid ester compound of thiophene and a halogenide of a phenyl group having an ortho substituent in the presence of a Pd catalyst.

Since a compound according to an embodiment of the present invention includes many thiophene rings in its core portion, a coupling reaction between one or two thiophene rings and the cage portion may be performed to synthesize an intermediate, and a coupling reaction between the intermediates may be performed to synthesize the compound.

[Chem. 9]

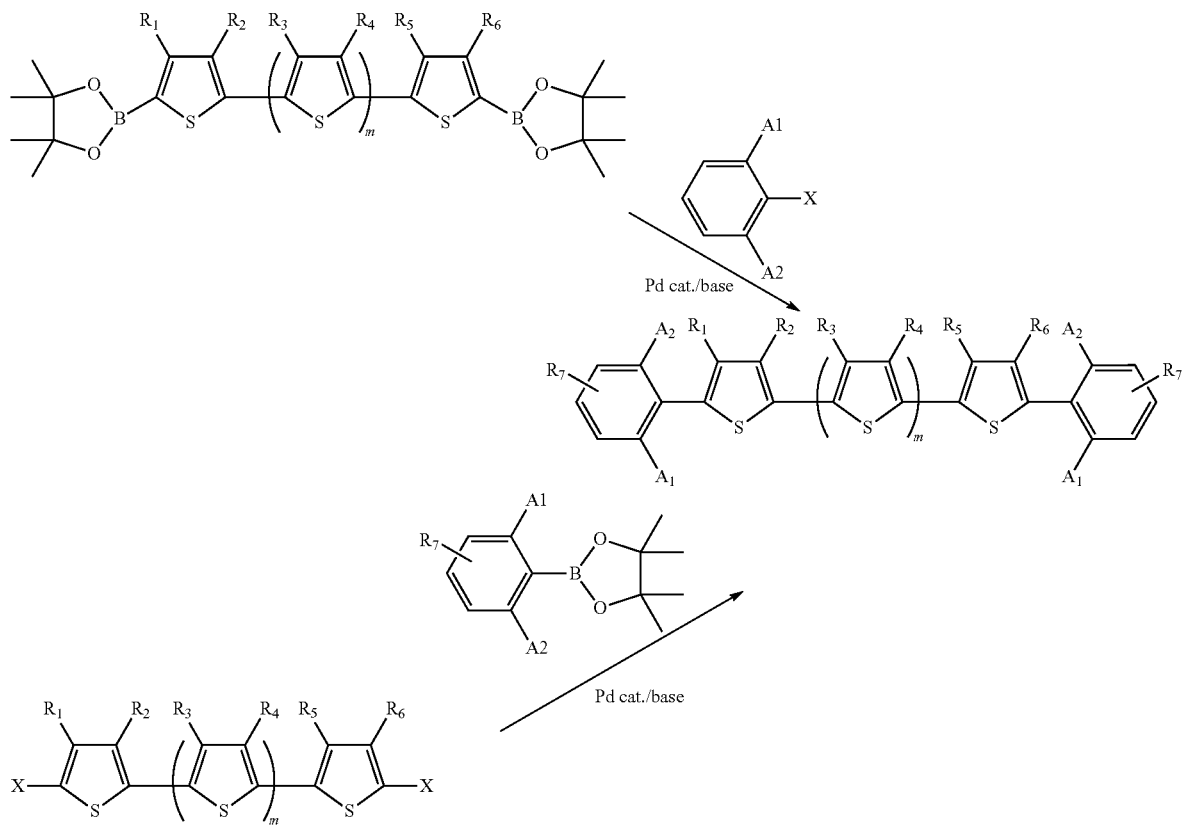

An electrochromic material according to an embodiment of the present invention may be used in known electrochromic elements.

For example, an electrochromic element includes a pair of electrodes and an electrochromic layer and an electrolyte layer between the pair of electrodes.

An organic compound according to an embodiment of the present invention may be deposited on an electrode to form a solid electrochromic layer. Alternatively, an organic compound according to an embodiment of the present invention may be dissolved in an electrolyte solution to form a solution phase.

In the case of the solid electrochromic layer, a method for depositing an organic compound according to an embodiment of the present invention on an electrode substrate is not particularly limited. An organic compound according to an embodiment of the present invention may be dissolved in an appropriate solvent and may be formed into a thin film by a known coating method (for example, spin coating, dipping, casting, a LB process, or an inkjet method), vacuum evaporation, ionized deposition, sputtering, or plasma deposition.

In the case of the solution electrochromic layer, an organic compound and a supporting electrolyte according to an embodiment of the present invention dissolved in an appropriate solvent (for example, an organic polar solvent, such as water, ethanol, propylene carbonate, ethylene carbonate, dimethyl sulfoxide, γ-butyrolactone, or acetonitrile) are injected between a pair of electrode substrates to form an element.

A composition 12 according to the present embodiment may contain a compound having the general formula [1] and a compound (a) having an absorption peak at 400 nm or more and 600 nm or less in its colored state.

The composition 12 may contain a compound having the general formula [1] in which m is 1 and the compound (a) having an absorption peak at 400 nm or more and 600 nm or less in its colored state.

The compounds having the general formula [1] and the compounds having the general formula [1] in which m is 1 are collectively referred to as compounds having a general formula [7].

In other words, the compounds having the general formula [7] are the compounds having the general formula [1] in which m is an integer in the range of 1 to 3.

When a compound having the general formula [7] is referred to as a compound (b), a composition according to the present embodiment may contain the compound (a) and the compound (b).

Specific examples of the compounds having the general formula [7] in which m is 1 include compounds of the following group C.

[Chem. 10]
C-1
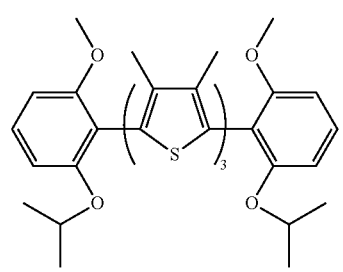
C-2
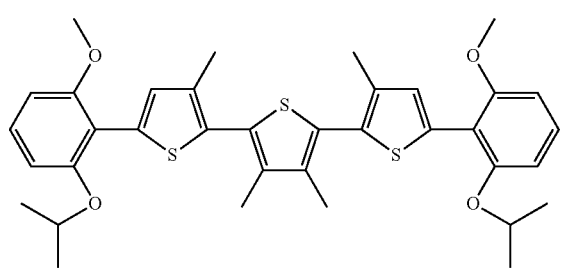
C-3
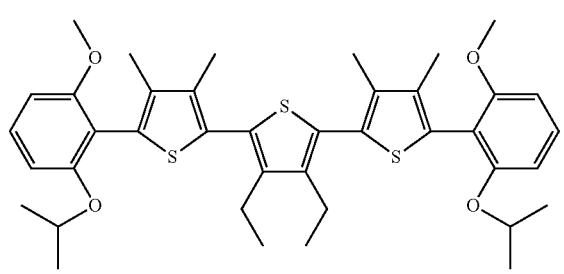
C-4
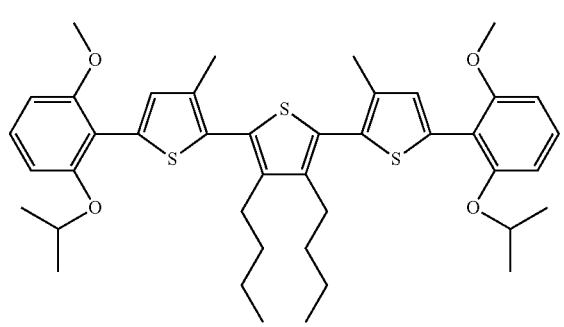
C-5
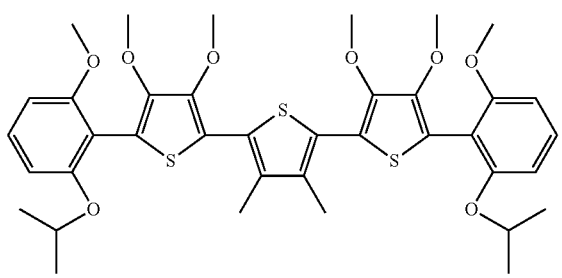
C-6
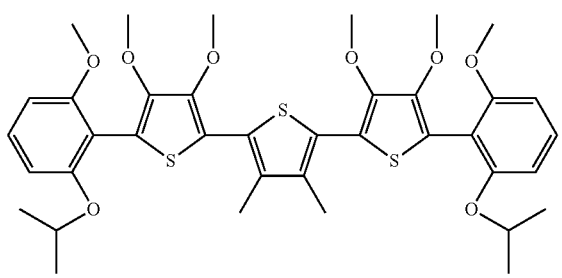
[Chem. 11]
C-7
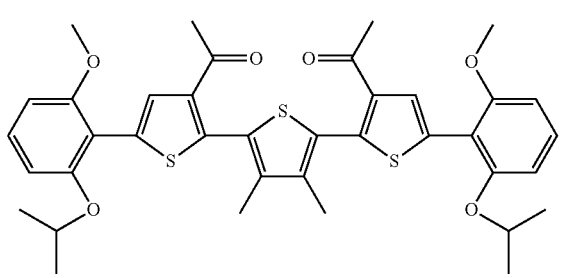
C-8
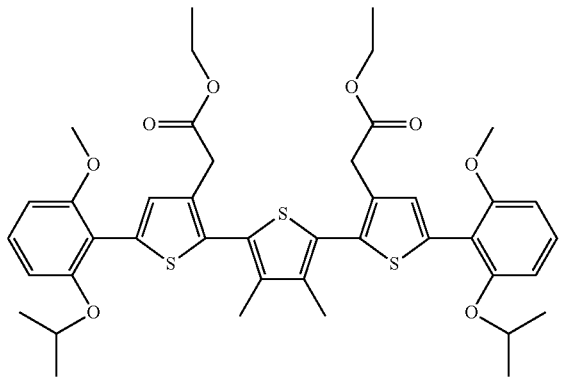
C-9
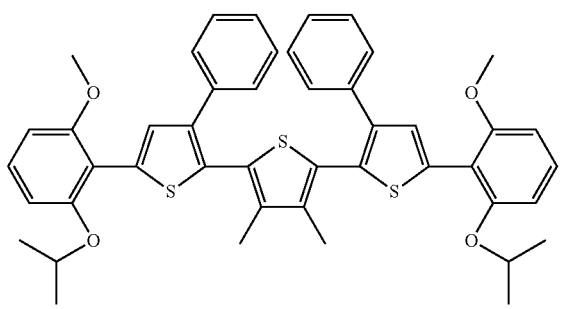

C-10
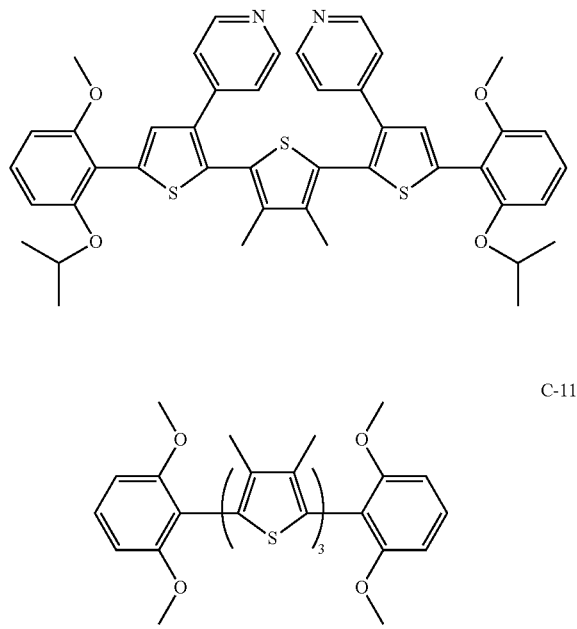

C-11
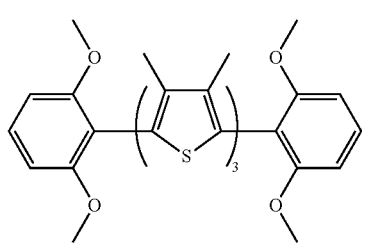

C-15
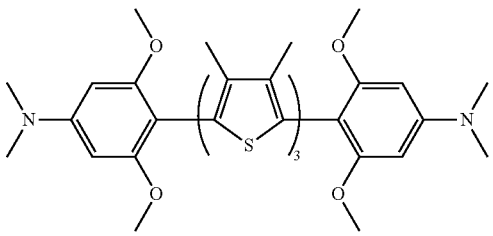

C-16
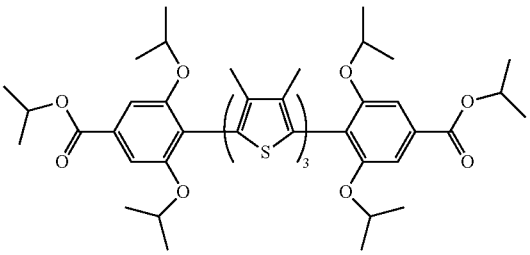

C-12
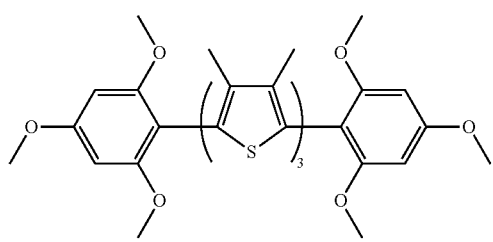

[Chem. 12]

C-13
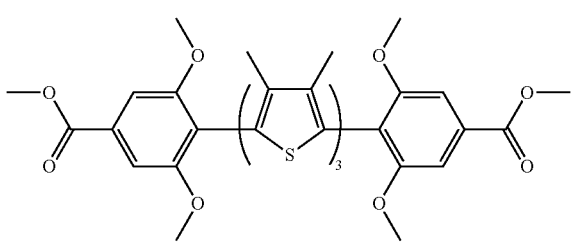

C-14
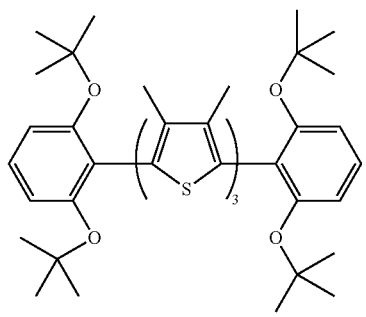

The compound (a) having an absorption peak at 400 nm or more and 600 nm or less in its colored state may be a known EC compound.

Examples of such compounds include thiophene derivatives, pyrrole derivatives, thiazine derivatives, triallylmethane derivatives, bisphenylmethane derivatives, ferrocene derivatives, xanthene derivatives, fluorane derivatives, and spiropyran derivatives.

Among these compounds, EC compounds (a) having absorption in a visible short wavelength region in its colored state may be thiophene compounds. Thiophene compounds have oxidation potential close to the oxidation potential of EC compounds (b) having absorption in a visible long wavelength region in its colored state.

A large difference in oxidation potential results in a large difference in the susceptibility of the EC compounds to oxidation or the oxidation speed of the EC compounds, making it difficult to control color balance in the colored state.

In particular, gray or black coloring in the colored state requires transmittance flatness due to uniform absorption in the entire visible light region. Thus, the compound (a) and the compound (b) may be combined.

The term "transmittance flatness", as used herein, means a small difference between the average transmittance and each transmittance in the wavelength region of 400 nm or more and 700 nm or less.

The thiophene compounds may be compounds having the following general formula [2], which have a skeleton similar to the skeleton of the EC compounds (b).

[Chem. 13]

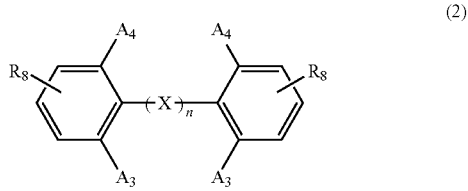

(2)

wherein A3 and A4 independently denote a hydrogen atom, an alkyl group containing 1 or more and 20 or less carbon atoms, an alkoxy group containing 1 or more and 20 or less carbon atoms, or an optionally substituted aryl group.

At least one of A3 and A4 denotes the alkyl group, the alkoxy group, or the aryl group. The aryl group may have an alkyl group containing 1 or more and 4 or less carbon atoms or an alkoxy group containing 1 or more and 4 or less carbon atoms as a substituent.

R8 denotes a hydrogen atom, a halogen atom, an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group. The aryl group may have an alkyl group containing 1 or more and 4 or less carbon atoms as a substituent.

In the general formula [2], X has a structure represented by any of the following general formulae [3] to [6], and n is 1 or 2. When n is 2, a plurality of X's are independently selected from the following general formulae [3] to [6]:

[Chem. 14]

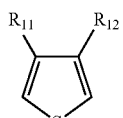

[3]

[Chem. 15]

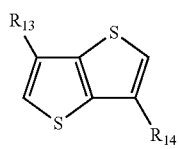

[4]

[Chem. 16]

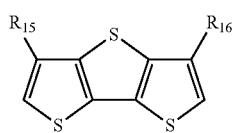

[5]

[Chem. 17]

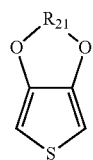

[6]

wherein R11 to R16 independently denote a hydrogen atom, a halogen atom, an alkyl group containing 1 or more and 20 or less carbon atoms, an alkoxy group containing 1 or more and 20 or less carbon atoms, an optionally substituted aryl group, an alkyl ester group containing 1 or more and 20 or less carbon atoms, an optionally substituted amino group, or a cyano group.

R21 denotes an optionally branched alkylene group having 1 or more and 20 or less carbon atoms.

The specific structural formula of the thiophene EC compound (a) will be described below. An EC compound according to an embodiment of the present invention is not limited to these.

[Chem. 18]

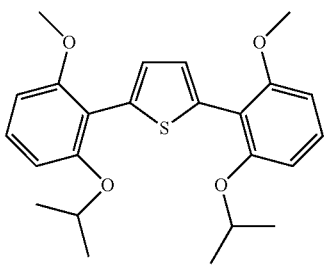

D-1

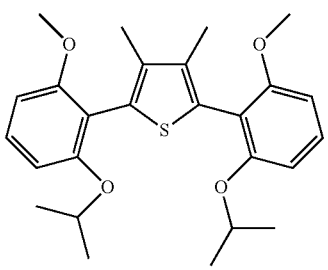

D-2

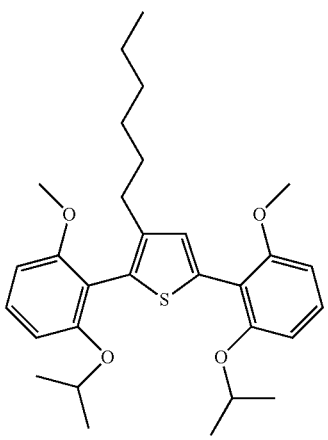

D-3

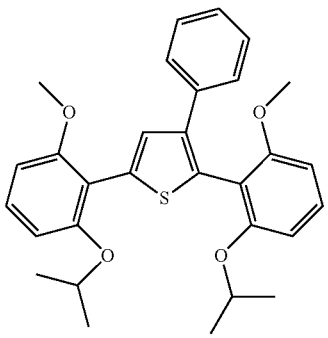

D-4

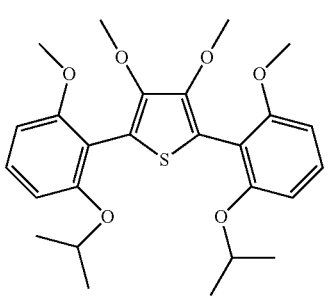

D-5

D-6
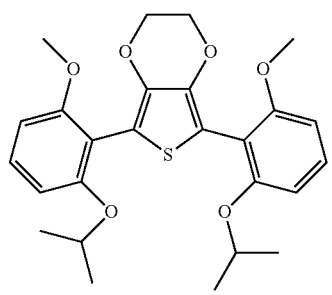
[Chem. 19]
D-7
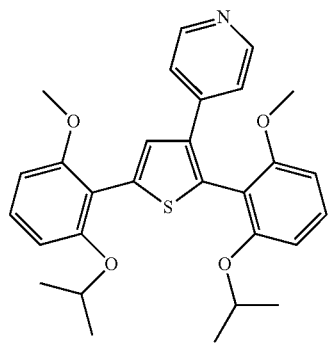
D-8
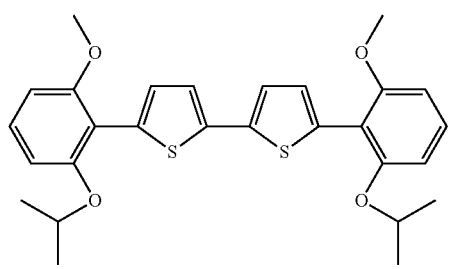
D-9
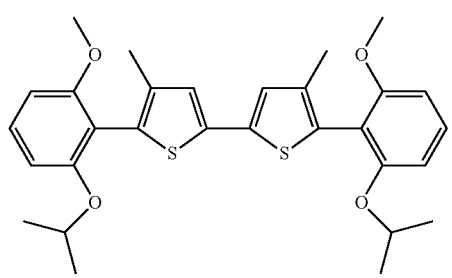
D-10
D-11
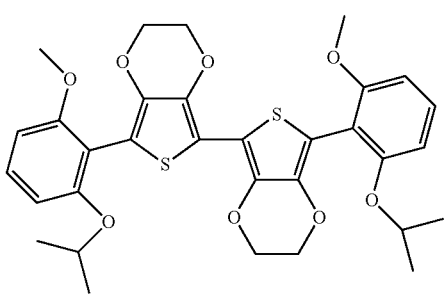
D-12
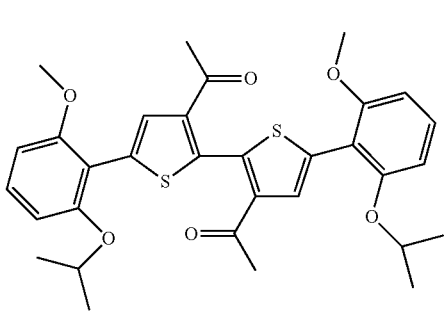
[Chem. 20]
D-13
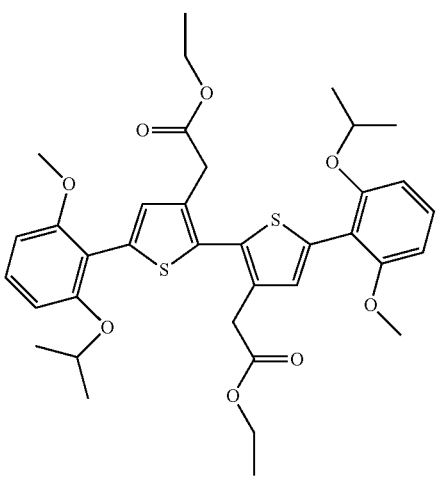
D-14
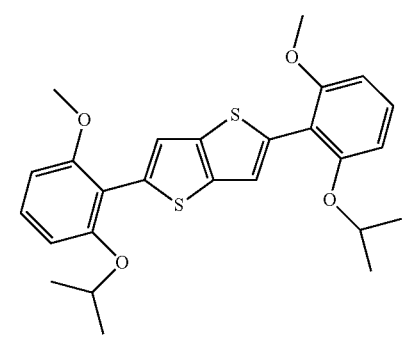

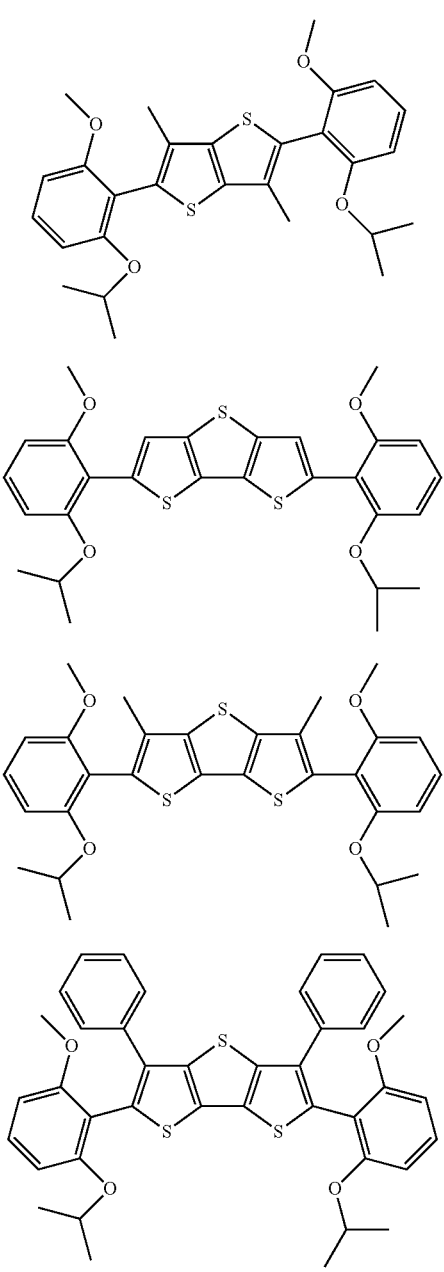

D-15

D-16

D-17

D-18

In the exemplary compounds of the group D, the core portion X having EC characteristics in the general formula [2] has various structures represented by the general formulae [3] to [6].

In the exemplary compounds of the group D, the substituents A3 and A4 in the terminal unit of the cage portion are a methoxy group and an isopropoxy group.

In addition to the methoxy group and the isopropoxy group, the terminal units A3 and A4 may be any substituents having an enough excluded volume to protect the core portion X having EC characteristics.

Examples of the substituents A3 and A4 are the same as the examples for the exemplary compound group B of the EC compounds (b).

In the compounds of the group D, n in the general formula [2] is 1 or 2, and the core portion is composed of one or two thiophene rings.

This short π-conjugated system results in absorption in a short to middle wavelength range of approximately 400 to 600 nm in the visible light region even in the oxidized colored state due to voltage application, as well as a short absorption wavelength and high transparency in the colorless state.

Thus, an EC element that has a composition containing an EC compound (a) having an oxidation absorption peak in the range of 400 to 600 nm and an EC compound (b) having an absorption peak in a visible long wavelength region or near-infrared region of 550 nm or more can be sufficiently colorless and transparent in the colorless state and absorb light in the entire visible light region to turn black in the colored state.

As in the cage effect of the terminal units in the compound group (b), the compound group (a) includes a substituted phenyl group having the steric hindrance portions A3 and A4, which protect the thiophene skeleton utilizing their steric hindrance.

When these compounds are used as EC materials, the resulting EC elements also have high durability in repetitive oxidation-reduction reactions.

Electrochromic Element According to Present Embodiment

An electrochromic element according to the present embodiment includes a pair of electrodes and an electrochromic layer between the pair of electrodes.

The electrochromic layer contains an electrochromic compound and a supporting electrolyte. The EC layer may include an EC compound layer and a supporting electrolyte layer. The EC layer may be formed of a solution containing an EC compound and a supporting electrolyte.

The composition 12 according to the present embodiment may contain a third EC compound in addition to the EC compounds (a) and (b).

Since the EC compounds (a) and (b) are colored by oxidation, upon voltage application, the EC compounds (a) and (b) lose an electron in an electrochemical reaction on a first electrode (anode) of an EC element.

The third EC compound is a reduction-coloring EC compound, which is colored on a second electrode (cathode) facing the first electrode in the EC element.

Examples of the reduction-coloring EC compound include viologen compounds, phenazine compounds, and phenoxazine compounds.

The addition of the reduction-coloring EC compound to a plurality of oxidation-coloring EC compounds selected from the EC compounds (a) and (b) can enhance the transmittance flatness of the EC element over the entire visible light region in the colored state.

The compounds (a) and (b) according to an embodiment of the present invention may be synthesized by a coupling reaction in the presence of a known Pd catalyst.

The EC organic compounds (a) and (b) according to the present embodiment may be synthesize by a coupling reaction in the presence of a Pd catalyst between a compound halogenide forming the core portion having EC characteristics and a boronic acid or boronic acid ester compound of a compound forming the terminal units or between a boronic acid or boronic acid ester compound of a compound forming the core portion having EC characteristics and a compound halogenide forming the terminal units.

As an example of the synthesis method, the following is a synthesis scheme of a compound that corresponds to the compound (a) and includes dithienothiophene as a core portion having EC characteristics.

In the synthesis scheme, X denotes a halogen atom, and A3 and A4 are substituents of a terminal unit phenyl group.

The dithienothiophene portion may be replaced by another EC organic compound to synthesize an EC organic compound according to the present embodiment.

Since the EC compounds (b) include many thiophene rings in their core portions, a coupling reaction between one or two thiophene rings and the terminal unit cage portion may be performed to synthesize an intermediate, and a coupling reaction between the intermediates may be performed to synthesize the EC compounds (b).

[Chem. 21]

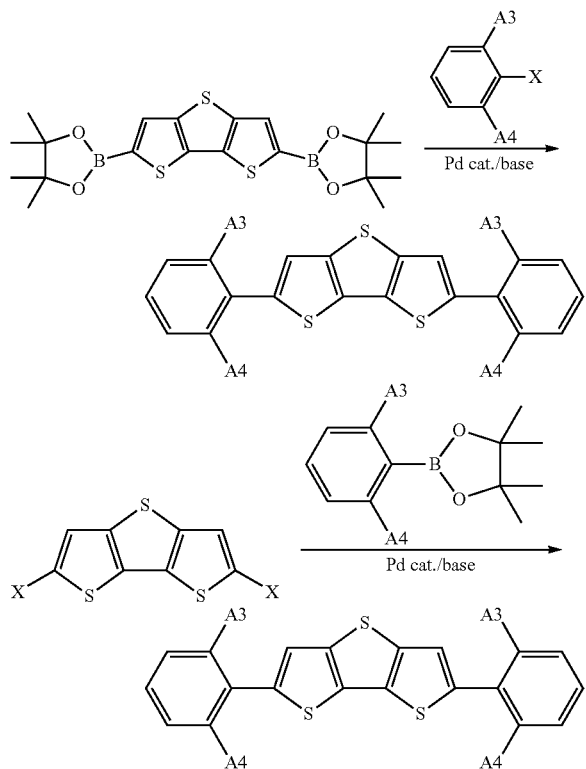

A first EC element according to the present embodiment is an EC element that includes a liquid 12 containing anodic EC compounds (a) and (b) dissolved in a solvent. The anodic EC compounds (a) and (b) can be colored by oxidation.

A second EC element according to the present embodiment is an EC element that includes a liquid 12 containing an anodic EC compound and a reduction-coloring cathodic EC compound, such as viologen, dissolved in a solvent.

The first EC element is referred to as a unipolar element, and the second EC element is referred to as a bipolar element.

The operation of the bipolar element generates a radical cation due to an oxidation reaction on one electrode and a radical cation due to reduction on the other electrode.

These radical cations diffuse in the solution and collide with each other to cause an oxidation-reduction reaction.

Because of the oxidation-reduction reaction outside the electrodes, the two radical cations disappear and return to their original substances and turn colorless.

Since the coloring reaction rate must be higher than this discoloring reaction rate, the oxidation-reduction reaction rate must be higher on the electrodes than in the liquid.

This requires a higher electric current and higher power consumption than unipolar elements. Thus, the EC element according to the present embodiment may be the unipolar EC element.

The components of the EC element according to the present embodiment will be described below. The EC compounds (a) and (b) as well as the electrolyte and the solvent in the liquid contained in the EC element will be described below.

The electrolyte may be any ionic dissociative salt that has high solubility in a solvent and high compatibility in a solid electrolyte. The ionic dissociative salt may be an electron-donating ionic dissociative salt.

Examples of the supporting electrolyte include inorganic ionic salts, such as alkali metal salts and alkaline-earth metal salts, quaternary ammonium salts, and cyclic quaternary ammonium salts.

More specifically, examples of the supporting electrolyte include alkali metal salts of Li, Na, and K, such as $LiClO_4$, LiSCN, $LiBF_4$, $LiAsF_6$, $LiCF_3SO_3$, $LiPF_6$, LiI, NaI, NaSCN, $NaClO_4$, $NaBF_4$, $NaAsF_6$, KSCN, and KCl, quaternary ammonium salts, such as $(CH_3)_4NBF_4$, $(C_2H_5)_4NBF_4$, $(n-C_4H_9)_4NBF_4$, $(C_2H_5)_4NBr$, $(C_2H_5)_4NClO_4$, and $(n-C_4H_9)_4NClO_4$, and cyclic quaternary ammonium salts.

The solvent for dissolving the EC organic compound and the supporting electrolyte may be any solvent that can dissolve the EC organic compound and the supporting electrolyte, particularly polar solvents.

Specific examples of the solvent include organic polar solvents, such as water, methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propiononitrile, benzonitrile, dimethylacetamide, methylpyrrolidinone, and dioxolane.

A polymer or a gelling agent may be added to the EC medium to increase the viscosity of the EC medium or form a gel.

Examples of the polymer include, but are not limited to, polyacrylonitrile, carboxymethylcellulose, poly(vinyl chloride), poly(ethylene oxide), poly(propylene oxide), polyurethane, polyacrylate, polymethacrylate, polyamide, polyacrylamide, polyester, and Nafion (registered trademark).

A transparent substrate and a transparent electrode will be described below. Transparent substrates 10 may be made of colorless or colored glass, tempered glass, or colorless or colored transparent resin.

More specifically, the transparent substrates 10 may be made of poly(ethylene terephthalate), poly(ethylene naphthalate), polynorbornene, polyamide, polysulfone, polyethersulfone, polyetheretherketone, poly(phenylene sulfide), polycarbonate, polyimide, or poly(methyl methacrylate).

Electrodes 11 may be made of a metal or metal oxide, such as an indium tin oxide (ITO) alloy, fluorine-doped tin oxide (FTO), tin oxide (NESA), indium zinc oxide (IZO), silver oxide, vanadium oxide, molybdenum oxide, gold, silver, platinum, copper, indium, or chromium, a silicon material, such as polycrystalline silicon or amorphous silicon, or a carbon material, such as carbon black, graphite, or glassy carbon.

The electrodes 11 may be made of an electrically conductive polymer having improved electric conductivity due to doping (for example, polyaniline, polypyrrole, polythiophene, polyacetylene, poly(p-phenylene), or a complex of polyethylenedioxythiophene (PEDOT) and poly(styrene sulfonate)).

An optical filter according to the present embodiment must be transparent. Thus, the electrodes 11 may be made of ITO, FTO, IZO, NESA, or an electrically conductive polymer having improved electric conductivity each having no optical absorption in the visible light region. The electric conductivity may be improved by a known method.

These electrode materials may be of various forms, such as a bulk or fine particles. These electrode materials may be used alone or in combination.

Spacers 13 between the electrodes 11 provide a space for the composition 12 that contains the EC compounds (a) and (b). More specifically, the spacers 13 may be made of polyimide, Teflon (registered trademark), a fluorocarbon rubber, or an epoxy resin. The spacers 13 can maintain the interelectrode distance of the EC element.

The EC element according to the present embodiment may include a liquid inlet formed by the electrodes and the spacer. After a composition containing an EC organic compound is charged through the inlet, the inlet may be sealed with a sealing member and may be hermetically sealed with an adhesive to produce the element.

The sealing member also serves to separate the adhesive from the EC organic compound. The sealing member may have any shape and may taper down to its tip like a wedge.

The EC element according to the present embodiment may be formed by any method. For example, the liquid 12 containing the EC compounds (a) and (b) may be injected into the space between the electrode substrates by vacuum injection, atmospheric injection, or a meniscus method.

The EC element according to the present embodiment may be used in optical filters, lens units, and image pickup apparatuses.

The EC element according to the present embodiment can have sufficiently high transparency in the colorless state and absorb light in the entire visible light region in the colored state, thus realizing black coloring with high transmittance flatness.

Because of its high durability, the EC element can be suitably used to control the amount of incident light and the incident wavelength distribution characteristics in an image pickup element, such as a camera. The incident wavelength distribution control is effective for color temperature conversion during picture taking. EC elements having high transmittance flatness can be suitably used as ND filters.

In particular, since a compound according to an embodiment of the present invention in the colored state has absorption at 600 nm or more in the visible light region to the near-infrared region, the compound is effectively used in filters in these wavelength regions.

More specifically, the EC element can be installed in an optical path of an imaging optical system connected to an image pickup element to control the amount of incident light and the incident wavelength distribution characteristics in the image pickup element.

The imaging optical system may be also referred to as a lens system. The imaging optical system may be a lens unit including a plurality of lenses.

An optical filter according to the present embodiment can be used to install an EC element in an optical path of an optical system (lens system) connected to an image pickup element to control the amount of incident light and the incident wavelength distribution characteristics in the image pickup element.

The EC element according to the present embodiment connected to a transistor can function as an optical filter. Examples of the transistor include TFT elements and MIM elements.

An image pickup apparatus according to the present embodiment includes an image pickup element and an imaging optical system including an optical filter. The EC element of the image pickup apparatus may be disposed in front of the imaging optical system or immediately in front of the image pickup element.

The EC element in the colorless state has high transparency and allows a sufficient amount of incident light to pass through. The EC element in the colored state can block and modulate incident light. The EC element has a long life because of its high durability in repetitive oxidation-reduction reactions.

EXAMPLES

Although the present invention will be further described in the following examples, the present invention is not limited to these examples.

Example 1

Synthesis of Exemplary Compound A-1

[Chem. 22]

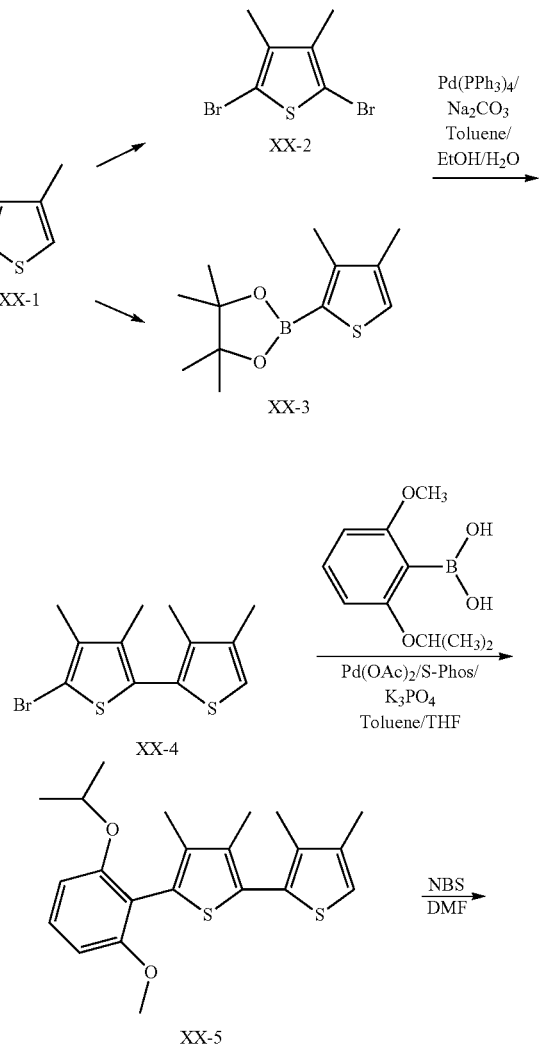

[Chem. 23]

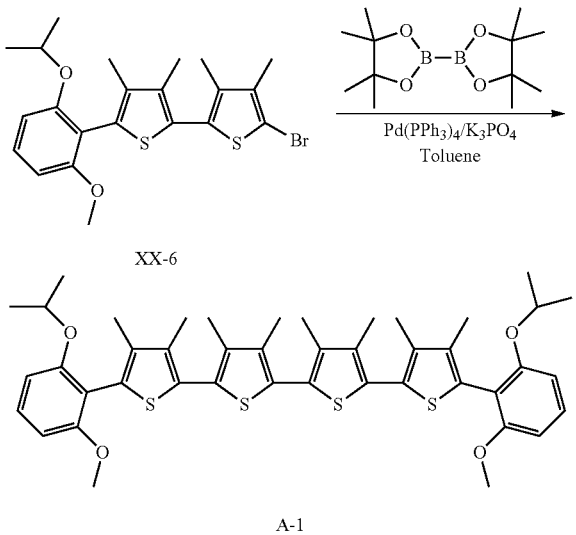

(1) 5.0 g (44.6 mmol) of XX-1 (3,4-dimethylthiophene) was dissolved in 80 ml of N,N-dimethylformamide (DMF) in a 300-mL reaction vessel. 31.7 g (178 mmol) of N-bromosuccinimide was then added to the solution. The solution was stirred at room temperature for one hour.

XX-1 was synthesized by a method described in Synthetic Communications, 2007, 37, 71.

Water was added to the reaction solution. The reaction solution was subjected to extraction with diethyl ether/hexane (1/1). The extract was washed with water and was concentrated under reduced pressure to yield a colorless liquid XX-2 (10.4 g).

(2) 2.55 g (22.7 mmol) of XX-1 (3,4-dimethylthiophene) was dissolved in 30 ml of diethyl ether in a 100-ml reaction vessel. The solution was cooled to −78° C.

18.2 ml of n-butyllithium (1.62 M hexane solution) was added dropwise to the solution. The solution was stirred at −78° C. for one hour.

5.92 g (31.8 mmol) of 2-isopropoxy-4,4,5,5-tetramethyl-1,3,2-dioxaborolane was then added to the solution. After 30 minutes, the reaction solution was returned to room temperature and was stirred at room temperature for two hours.

Aqueous ammonium chloride was added to the solution to terminate the reaction. The solution was subjected to extraction with diisopropyl ether. The ether layer was washed with water and was concentrated under reduced pressure to yield a crude product.

The crude product was separated and purified by silica gel chromatography (mobile phase: heptane/toluene=1/1) to yield a colorless liquid XX-3.

(3) 3.0 g (11.1 mmol) of XX-2 and 3.0 g (7.56 mmol) of XX-3 were mixed in a toluene/ethanol/distilled water (30 ml/15 ml/30 ml) mixed solvent in a 100-ml reaction vessel. Dissolved oxygen was removed using nitrogen.

0.38 g (0.333 mmol) of Pd(PPh₃)₄ and 3.5 g (33.3 mmol) of sodium carbonate were then added to the mixture in a nitrogen atmosphere. The mixture was then allowed to react at 70° C. for 14 hours and then at 90° C. for 10 hours.

The reaction solution was cooled to room temperature, was concentrated under reduced pressure, and was separated and purified by silica gel chromatography (mobile phase: heptane) to yield a colorless solid XX-4 (1.12 g).

(4) 1.12 g (3.72 mmol) of XX-4 and 1.02 g (4.83 mmol) of 2-isopropoxy-6-methoxyphenylboronic acid were mixed in a toluene/tetrahydrofuran (15 ml/5 ml) mixed solvent in a 50-ml reaction vessel. Dissolved oxygen was removed using nitrogen.

28.1 mg (0.112 mmol) of Pd(OAc)₂ and 153 mg (0.372 mmol) of 2-dicyclohexylphosphino-2',6'-dimethoxybiphenyl (S-Phos) were added to the mixture in a nitrogen atmosphere. The mixture was allowed to react at 110° C. for 24 hours under reflux. The reaction solution was cooled to room temperature, was concentrated under reduced pressure, and was separated and purified by silica gel chromatography (mobile phase: heptane/ethyl acetate=10/1) to yield a colorless solid XX-5 (1.26 g).

(5) 1.26 g (3.26 mmol) of XX-5 was dissolved in 15 ml of DMF in a 100-mL reaction vessel. 0.638 g (3.59 mmol) of N-bromosuccinimide was then added to the solution. The solution was stirred at room temperature for two hours.

Water was added to the reaction solution. The reaction solution was then subjected to extraction with ethyl acetate. The extract was washed with water, was concentrated under reduced pressure, and was separated and purified by silica gel chromatography (mobile phase: heptane/ethyl acetate=10/1) to yield XX-6 (1.19 g).

(6) 1.0 g (2.15 mmol) of XX-6 and 0.33 g (1.29 mmol) of bis(pinacolato)diboron were dissolved in 20 ml of toluene in a 50-ml reaction vessel. Dissolved oxygen was removed using nitrogen.

0.24 g (0.215 mmol) of Pd(PPh₃)₄ and 0.912 g (4.30 mmol) of tripotassium phosphate were added to the solution in a nitrogen atmosphere. The solution was allowed to react at 100° C. for 18 hours under reflux.

The reaction solution was cooled to room temperature, was concentrated under reduced pressure, and was separated and purified by silica gel chromatography (mobile phase: heptane/ethyl acetate=5/1) to yield a white solid powder A-1 (0.61 g).

The structure of the compound A-1 was analyzed in mass spectrum (MS) measurement and nuclear magnetic resonance spectrum (NMR) measurement. The molecular weight and the NMR peak integral ratio agreed with the structure of the compound A-1.

More specifically, the $M^+$ of the compound was confirmed to be 770 in matrix-assisted laser desorption ionization mass spectrum (MALDI-MS) measurement. The NMR spectrum measurement results are as follows:

$^1$H-NMR (CDCl₃)σ(ppm): 7.25 (t, 2H), 6.65 (d, 2H), 6.62 (d, 2H), 4.37 (sept, 2H), 3.79 (s, 6H), 2.14 (s, 18H), 1.94 (s, 6H), 1.24 (d, 6H), 1.18 (d, 6H).

An exemplary method for synthesizing an EC organic compound according to the present embodiment will be described below. The structures of the thiophene derivative having EC characteristics (core portion) and the terminal unit cage portion in the synthesis example can be altered to synthesize a desired EC organic compound.

Example 2

Synthesis of Exemplary Compound C-1

[Chem. 24]

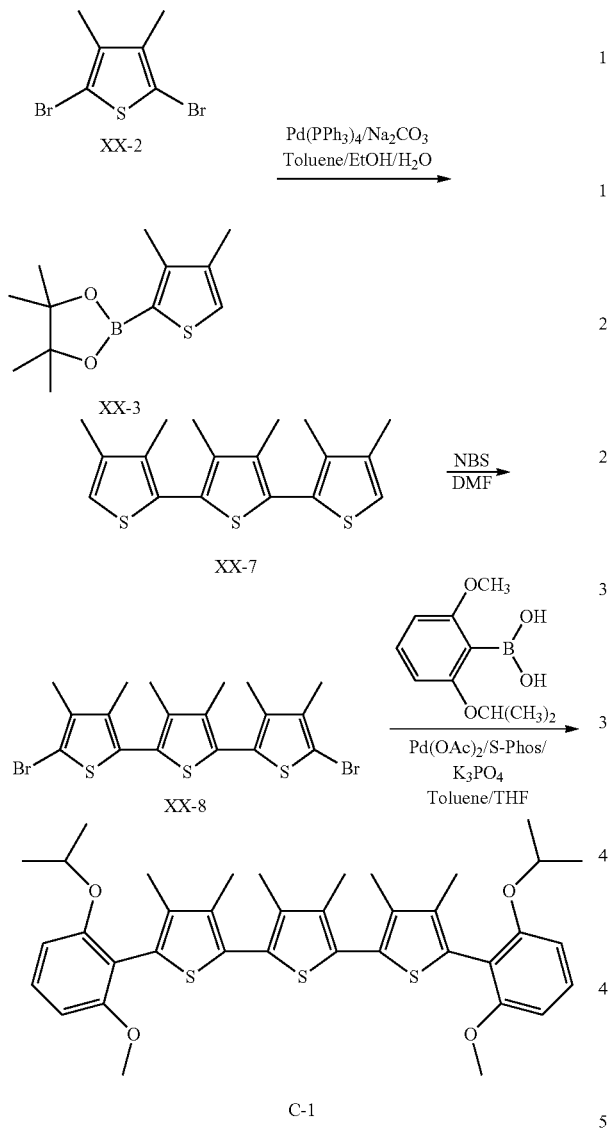

(1) 2.1 g (7.76 mmol) of XX-2 and 4.62 g (ca. 10 mmol) of XX-3 prepared in Example 1 were mixed in a toluene/ethanol/distilled water (25 ml/13 ml/25 ml) mixed solvent in a 200-ml reaction vessel. Dissolved oxygen was removed using nitrogen.

0.27 g (0.233 mmol) of Pd(PPh$_3$)$_4$ and 2.5 g (23.3 mmol) of sodium carbonate were then added to the mixture in a nitrogen atmosphere. The mixture was then allowed to react at 90° C. for 21 hours.

The reaction solution was cooled to room temperature, was concentrated under reduced pressure, and was separated and purified by silica gel chromatography (mobile phase: heptane) to yield a colorless viscous amorphous XX-7 (0.75 g).

(2) 1.95 g (5.86 mmol) of XX-7 was dissolved in 40 ml of DMF in a 100-mL reaction vessel. 2.71 g (15.2 mmol) of N-bromosuccinimide was then added to the solution. The solution was stirred at room temperature for six hours.

Water was added to the reaction solution. The resulting precipitate was dispersed and washed with methanol and was filtered off to yield XX-8 (2.54 g).

(3) 600 mg (1.22 mmol) of XX-8 and 771 mg (3.67 mmol) of 2-isopropoxy-6-methoxyphenylboronic acid were mixed in a toluene/tetrahydrofuran (6 ml/6 ml) mixed solvent in a 100-ml reaction vessel. Dissolved oxygen was removed using nitrogen.

11.0 mg (0.049 mmol) of Pd(OAc)$_2$, 50 mg (0.122 mmol) of 2-dicyclohexylphosphino-2',6'-dimethoxybiphenyl (S-Phos), and 1.41 g (6.12 mmol) of tripotassium phosphate were added to the mixture in a nitrogen atmosphere. The mixture was allowed to react at 110° C. for 13 hours under reflux.

The reaction solution was cooled to room temperature, was concentrated under reduced pressure, and was separated and purified by silica gel chromatography (mobile phase: hexane/chloroform=1/3) to yield a white solid powder C-1 (35 mg).

The M$^+$ of this compound was confirmed to be 660 in MALDI-MS measurement. The NMR spectrum measurement results are as follows:

$^1$H-NMR (CDCl$_3$)σ(ppm): 7.25 (t, 2H), 6.64 (d, 2H), 6.62 (d, 2H), 4.36 (sept, 2H), 3.79 (s, 6H), 2.14 (s, 6H), 2.13 (s, 6H), 1.94 (s, 6H), 1.24 (d, 6H), 1.19 (d, 6H).

Synthesis Example 1

Synthesis of Exemplary Compound D-2

[Chem. 25]

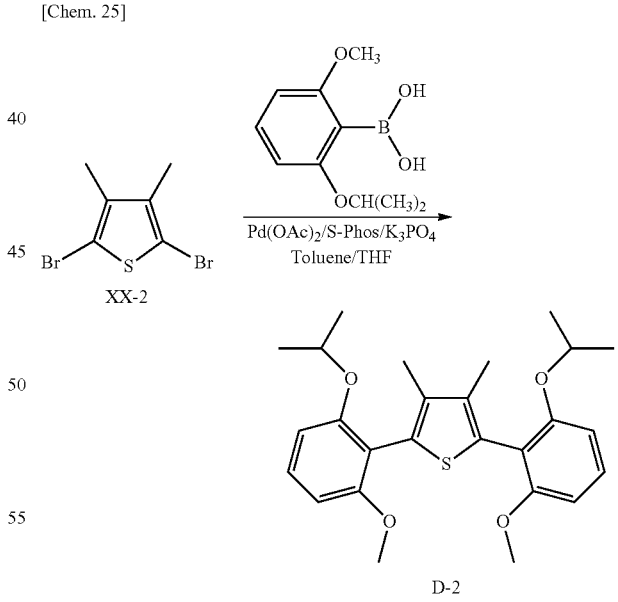

500 mg (1.85 mmol) of XX-2 and 1.17 g (5.56 mmol) of 2-isopropoxy-6-methoxyphenylboronic acid prepared in the synthesis example 1 were mixed in a toluene/tetrahydrofuran (5 ml/5 ml) mixed solvent in a 50-ml reaction vessel. Dissolved oxygen was removed using nitrogen.

16.6 mg (0.074 mmol) of Pd(OAc)$_2$, 76 mg (0.185 mmol) of 2-dicyclohexylphosphino-2',6'-dimethoxybiphenyl (S-Phos), and 2.13 g (9.26 mmol) of tripotassium phosphate were added to the mixture in a nitrogen atmosphere. The mixture was allowed to react at 100° C. for six hours under reflux.

The reaction solution was cooled to room temperature, was concentrated under reduced pressure, and was separated and purified by silica gel chromatography (mobile phase: hexane/ethyl acetate=5/2) to yield a colorless viscous liquid D-2 (510 mg).

The M⁺ of the compound was confirmed to be 440 in the NMR and MALDI-MS measurement in the same manner as in the synthesis example 1. The NMR spectrum measurement results are as follows:

$^1$H-NMR (CDCl$_3$)σ(ppm): 7.23 (t, 2H), 6.64 (d, 2H), 6.62 (d, 2H), 4.31 (sept, 2H), 3.78 (s, 6H), 1.94 (s, 6H), 1.18 (d, 6H), 1.12 (d, 6H).

Synthesis Example 2

Synthesis of Exemplary Compound D-6

[Chem. 26]

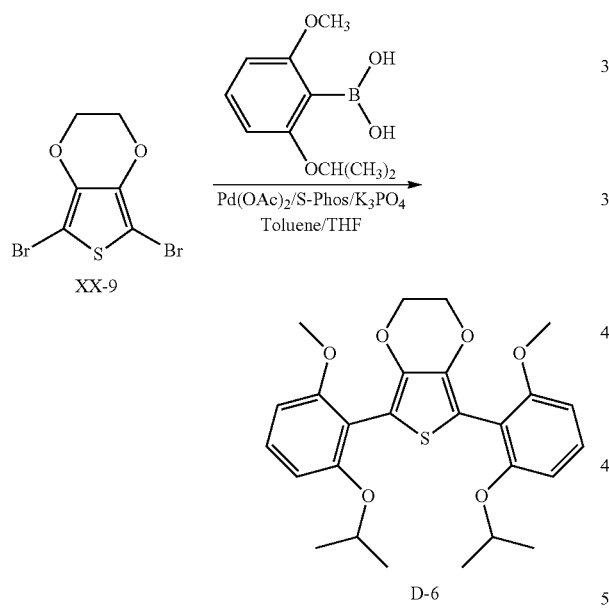

500 mg (1.67 mmol) of XX-9 (2,5-dibromoethylenedioxythiophene) and 1.05 g (5.0 mmol) of 2-isopropoxy-6-methoxyphenylboronic acid were mixed in a toluene/tetrahydrofuran (10 ml/5 ml) mixed solvent in a 50-ml reaction vessel. Dissolved oxygen was removed using nitrogen.

19 mg (0.083 mmol) of Pd(OAc)$_2$, 89 mg (0.22 mmol) of 2-dicyclohexylphosphino-2',6'-dimethoxybiphenyl (S-Phos), and 1.92 g (8.35 mmol) of tripotassium phosphate were added to the mixture in a nitrogen atmosphere. The mixture was allowed to react at 110° C. for seven hours under reflux.

The reaction solution was cooled to room temperature, was concentrated under reduced pressure, and was separated and purified by silica gel chromatography (mobile phase: hexane/ethyl acetate=4/3) to yield a white solid powder D-6 (420 mg, yield 54%).

The M⁺ of the compound was confirmed to be 470 in the MALDI-MS measurement in the same manner as in the synthesis example 1. The NMR spectrum measurement results are as follows:

$^1$H-NMR (CDCl$_3$)σ(ppm): 7.21 (t, 2H), 6.63 (d, 2H), 6.60 (d, 2H), 4.41 (m, 2H), 4.20 (s, 4H), 3.81 (s, 6H), 1.25 (s, 6H), 1.24 (s, 6H).

Synthesis Example 3

Synthesis of Exemplary Compound D-14

[Chem. 27]

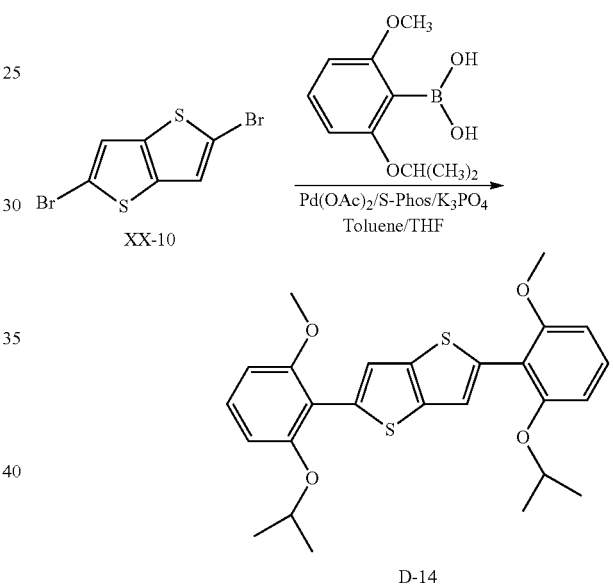

200 mg (0.671 mmol) of XX-10 and 563 mg (2.684 mmol) of 2-isopropoxy-6-methoxyphenylboronic acid were dissolved in a toluene/tetrahydrofuran (6 ml/3 ml) mixed solvent in a 50-ml reaction vessel. Dissolved oxygen was removed using nitrogen.

3.0 mg (0.013 mmol) of Pd(OAc)$_2$, 13.8 mg (0.034 mmol) of 2-dicyclohexylphosphino-2',6'-dimethoxybiphenyl (S-Phos), and 772 mg (3.36 mmol) of tripotassium phosphate were added to the solution in a nitrogen atmosphere. The solution was allowed to react at 110° C. for eight hours under reflux.

The reaction solution was cooled to room temperature, was concentrated under reduced pressure, and was separated and purified by silica gel chromatography (mobile phase: hexane/chloroform=1/2) to yield a white solid powder D-14 (235 mg, yield 75%). The M⁺ of this compound was confirmed to be 468 in MALDI-MS measurement.

Synthesis Example 4

Synthesis of Exemplary Compound D-16

[Chem. 28]

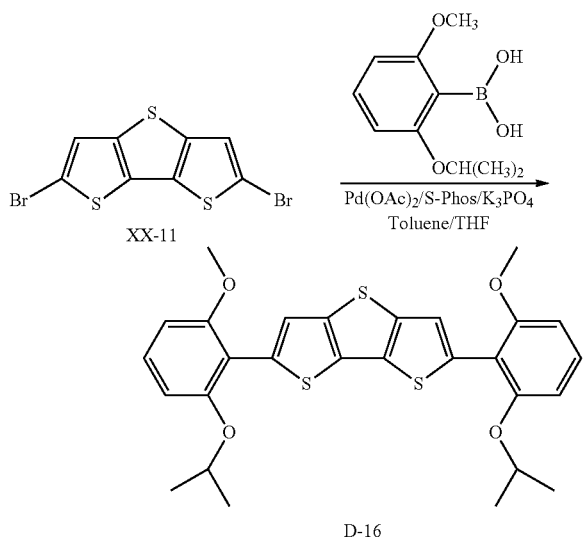

177.05 mg (0.50 mmol) of XX-11 and 420 mg (2.0 mmol) of 2-isopropoxy-6-methoxyphenylboronic acid were mixed in a toluene/tetrahydrofuran (6 ml/3 ml) mixed solvent in a 50-ml reaction vessel. Dissolved oxygen was removed using nitrogen.

2.3 mg (0.01 mmol) of Pd(OAc)$_2$, 10.3 mg (0.025 mmol) of 2-dicyclohexylphosphino-2',6'-dimethoxybiphenyl (S-Phos), and 575.7 mg (2.5 mmol) of tripotassium phosphate were added to the mixture in a nitrogen atmosphere. The mixture was allowed to react at 110° C. for eight hours under reflux.

The reaction solution was cooled to room temperature, was concentrated under reduced pressure, and was separate and purified by silica gel chromatography (mobile phase: hexane/chloroform=1/2) to yield a white solid powder D-16 (187 mg, yield 71%). The M$^+$ of this compound was confirmed to be 524 in MALDI-MS measurement.

Example 3

Evaluation of Electrochromic Characteristics

The absorption spectrum of a solution of the compound according to Example 1 dissolved in chloroform was measured in the neutral state (colorless state) with an ultraviolet-visible spectrophotometer (V-560 manufactured by JASCO Corp.).

Absorption spectra in the oxidized (colored) state were measured with a platinum working electrode, a platinum counter electrode, and a silver reference electrode. Each of the compounds according to the examples was dissolved in a supporting electrolyte tetrabutylammonium perchlorate solution (0.1 mol/L) dissolved in dichloroethane to prepare a solution (5.0×10$^{-4}$ mol/L).

The absorption spectrum and transmittance spectrum changes of the compound solution were measured using potentiostatic oxidation at the first oxidation potential of the compound or higher to examine the electrochromic characteristics of the compound.

Figure 3:
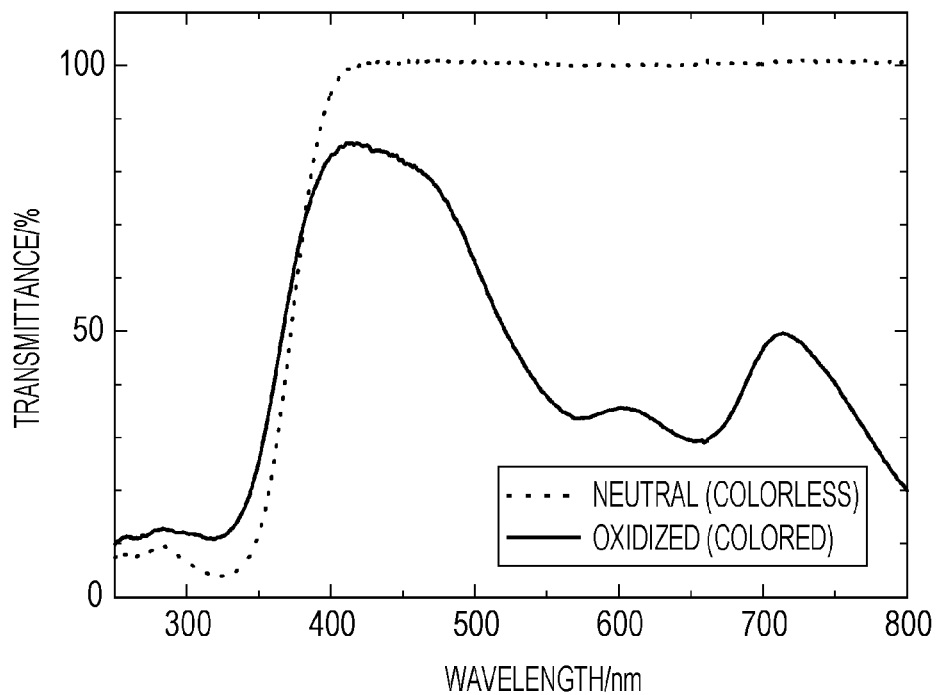
FIG. 3 is an ultraviolet-visible absorption spectrum indicating the electrochromic characteristics of an exemplary compound A-1 according to Example 3 of the present invention.

FIG. 3 shows the transmittance spectra of the compound A-1 in the neutral and oxidized states.

In the neutral state, the wavelength λmax of the maximum absorption peak was 319.0 nm in the ultraviolet region, and no absorption was observed over the entire visible light region. This indicates that the compound A-1 is a transparent material.

The colored compound produced by oxidation had a λmax of 652.4 nm, which is a long wavelength in the visible light region, and was visually colored. The oxidized colored state returned to the colorless transparent state by reduction. This indicates the electrochromic characteristics associated with oxidation-reduction.

Comparative Example 1

The λmax of the absorption of the following compound 3T-1 in its neutral and oxidized states described in David D. Graf and Kent R. Mann, Inorganic Chemistry, 1997, 36, 141 was shown in Table 2, together with the λmax of the compound A-1 according to Example 1.

[Chem. 29]

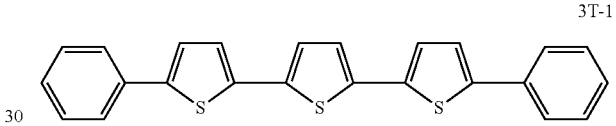

3T-1

TABLE 2

| Compound No. | Neutral λmax (nm) | Oxidized λmax (nm) |
|---|---|---|
| A-1 (Present invention) | 319 | 652 |
| 3T-1 (David D. Graf and Kent R. Mann, Inorganic Chemistry, 1997, 36, 141) | 408 | 662 |

In the oxidized colored state, the absorption wavelength of the compound 3T-1 was the same as the absorption wavelength of the compound A-1. In the neutral state, the compound A-1 had a shorter absorption wavelength than the compound 3T-1 and had higher transparency than the compound 3T-1.

<Evaluation of Electrochromic Characteristics>

Example 4

The absorption spectrum of each solution of the compounds according to the synthesis examples dissolved in chloroform was measured in the neutral state (colorless state) with an ultraviolet-visible spectrophotometer (V-560 manufactured by JASCO Corp.).

Absorption spectra in the oxidized (colored) state were measured with a platinum working electrode, a platinum counter electrode, and a silver reference electrode. Each of the compounds according to the synthesis examples was dissolved in a supporting electrolyte tetrabutylammonium perchlorate solution (0.1 mol/L) dissolved in dichloromethane to prepare a solution (5.0×10$^{-4}$ mol/L). The absorption spectrum and transmittance spectrum changes of the compound solution were measured using potentiostatic oxidation at the oxidation potential of the compound or higher. Table 3 shows the results.

TABLE 3

| Compound group | Compound No. | Neutral absorption λmax (nm) | oxidation absorption λmax (nm) |
|---|---|---|---|
| (a) | D-2 | 287.0 | 446.0 |
| | D-6 | 290.0 | 448.5 |
| | D-14 | 340.0 | 540.0 |
| | D-16 | 364.5 | 566.0 |
| (b) | C-1 | 311.5 | 593.3 |
| | A-1 | 319.0 | 652.4 |

In the neutral state, the wavelength λmax of the maximum absorption peak of any of the compounds was in the ultraviolet region, and no absorption was observed over the entire visible light region. This indicates that the compounds are transparent materials.

With respect to the colored compounds produced by oxidation, the compound group (a) had a λmax in the range of 446 to 566 nm, which is a short to middle wavelength range in the visible light region, and A-1 and C-1 of the compound group (b) had a λmax in the range of 593 to 652 nm, which is a long wavelength in the visible light region.

The compound groups (a) and (b) were visually colored in their oxidized state. The oxidized colored state returned to the colorless transparent state by reduction. This indicates the electrochromic characteristics associated with oxidation-reduction.

Example 5

<Oxidation Coloring of Composition>

The following three EC compounds were dissolved in a supporting electrolyte tetrabutylammonium perchlorate solution (0.1 mol/L) dissolved in dichloromethane to prepare an EC compound mixed solution. More specifically, the three EC compounds were D-6 (0.5 mM) and D-14 (0.071 mM) of the compound group (a) and A-1 (0.375 mM) of the compound group (b).

Figure 4:
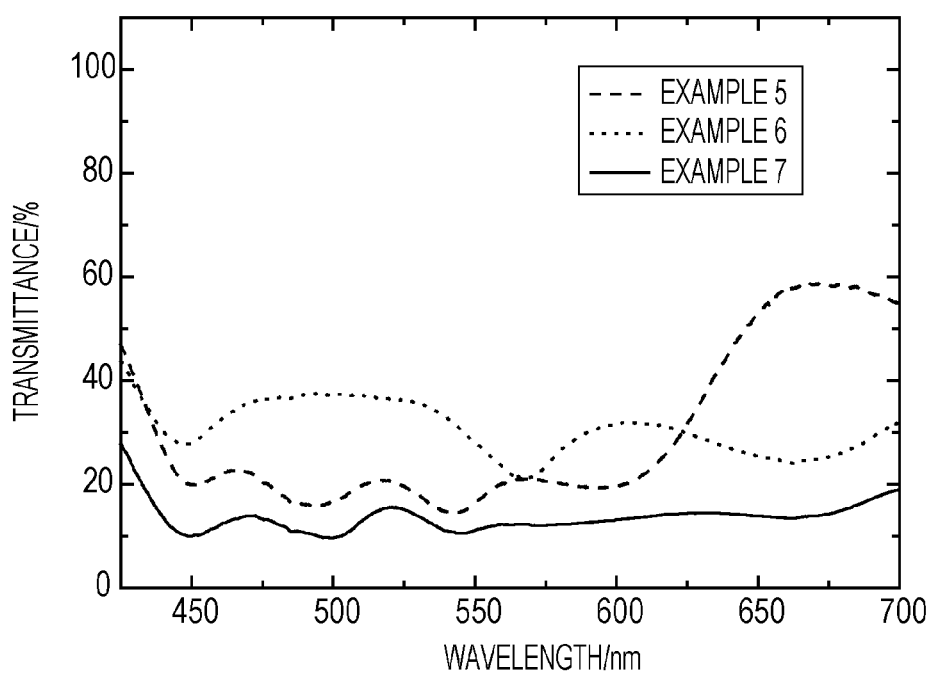
FIG. 4 is a transmittance spectrum of electrochromic compositions according to Examples 5 to 7 in their oxidized state.

The transmittance spectrum change of the mixed solution was measured using the three electrodes described in Example 4 in potentiostatic oxidation at the oxidation potential of the compound or higher. FIG. 4 shows the results.

Example 6

A solution was prepared in the same manner as in Example 5 except that the EC compounds in the EC compound mixed solution were the following three EC compounds. The transmittance spectrum of the solution was measured after potentiostatic oxidation.

The three EC compounds were D-2 (0.5 mM) and D-16 (0.083 mM) of the compound group (a) and C-1 (0.375 mM) of the compound group (b). FIG. 4 shows the results.

Example 7

A solution was prepared in the same manner as in Example 5 except that the EC compounds in the EC compound mixed solution were the following five EC compounds. The transmittance spectrum of the solution was measured after potentiostatic oxidation.

The five EC compounds were D-2 (0.325 mM), D-6 (0.455 mM), and D-14 (0.065 mM) of the compound group (a) and A-1 (0.13 mM) and C-1 (0.65 mM) of the compound group (b). FIG. 4 shows the results.

Examples 5 to 7 in the colorless state had no absorption in the visible light region and had high transparency. A combination of the EC compound groups (a) and (b) in the oxidized colored state can control the absorption band over the entire visible light region.

Example 7 had a sufficiently small difference between the average transmittance in the visible light region and transmittance in each wavelength, had satisfactory transmittance flatness, and was visually colored black.

Example 8 and Comparative Example 2

<Oxidation-Reduction Cycle Durability>

The oxidation-reduction cycle durability of an organic EC compound according to an embodiment of the present invention was evaluated. A representative example of the group (a) was D-16, a representative example of the group (b) was A-1, and a comparative example was a known reduction-coloring EC compound (diethylviologen diperchlorate) Ref-1. Ref-1 has the following structure:

[Chem. 30]

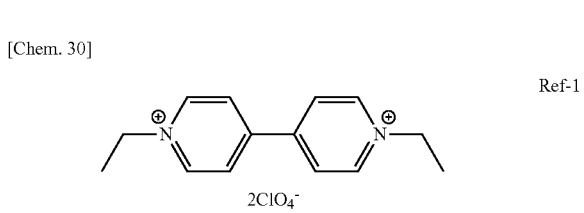

Ref-1

The durability was measured using a glassy carbon working electrode, a platinum counter electrode, and a silver reference electrode. Each of the compounds was dissolved in a supporting electrolyte tetrabutylammonium perchlorate solution (0.1 mol/L) dissolved in dichloromethane to prepare a solution ($1.0 \times 10^{-4}$ mol/L).

A rectangular wave potential program including potentiostatic oxidation at the oxidation potential of the compound or higher for 10 seconds and potentiostatic reduction at 0 V (vs. Ag/Ag+) for 10 seconds was performed with the solution 10000 times. An oxidation peak current change due to 10000 oxidation-reduction cycles of less than 20% as determined by cyclic voltammetry (CV) was judged to be passed (a circle mark), and an oxidation peak current change of 20% or more was judged to be failed (a cross mark). Table 4 shows the results.

TABLE 4

| Compound No. | Evaluation of durability |
|---|---|
| A-1 | ○ |
| D-16 | ○ |
| Ref-1 | X |

The compound Ref-1 according to the comparative example deteriorated after approximately 1600 oxidation-reduction cycles when the oxidation peak current decreased by 20%. The compounds A-1 and D-16 according to the examples of the present invention were stable after 10000 oxidation-reduction cycles when the oxidation peak current decreased by less than 20%.

Thus, the compounds according to the examples had higher oxidation-reduction cycle durability than Ref-1 according to the comparative example.

This is because bulky substituents protected the core portion that generated an unstable radical during oxidation. Furthermore, the phenyl group substituted by an electron-donating alkoxy group in the cage portion prevented the side reaction and degradation reaction of the core portion (radical cation), which lacks electrons during oxidation, thereby enhancing durability.

Accordingly, the present invention can provide an EC element formed of an EC composition that absorbs no light in the visible light region and is transparent in its colorless state and that absorbs light in the entire visible light region and is colored black in its colored state.

The present invention can also provide an EC element that has high durability under repeated oxidation and reduction.

An organic compound according to an embodiment of the present invention has high transparency with no optical absorption in the visible light region in its colorless state, absorbs light in a long wavelength region in its colored state, and is stable under repeated oxidation and reduction. Thus, the organic compound can be used in EC elements as well as optical filters, lens units, and image pickup apparatuses including the EC elements.

The present invention can provide an electrochromic organic compound that has high transparency with no optical absorption in the visible light region in its colorless state, absorbs light in a long wavelength region of 600 nm or more in its colored state, and is stable under repeated oxidation and reduction.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-222899, filed Oct. 5, 2012, which is hereby incorporated by reference herein in its entirety.

What is claimed is:

1. A composition, comprising a compound having an absorption peak at 400 nm or more and 600 nm or less in its colored state and a compound having the following general formula [7]:

[Chem. 2]

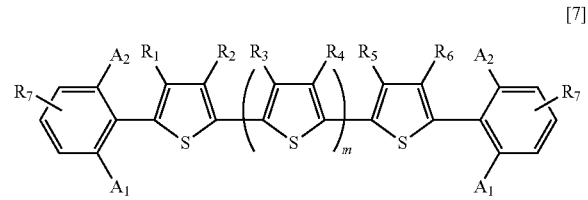

[7]

wherein $A_1$ and $A_2$ independently denote a hydrogen atom, an alkyl group containing 1 or more and 20 or less carbon atoms, an alkoxy group containing 1 or more and 20 or less carbon atoms, or an optionally substituted aryl group, provided that at least one of $A_1$ and $A_2$ denotes the alkyl group, the alkoxy group, or the aryl group, the aryl group may have an alkyl group containing 1 or more and 8 or less carbon atoms or an alkoxy group containing 1 or more and 8 or less carbon atoms as a substituent, $R_7$ denotes a hydrogen atom, a halogen atom, an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group, the aryl group may have an alkyl group containing 1 or more and 4 or less carbon atoms as a substituent, $R_2$ to $R_5$ independently denote an alkyl group containing 1 or more and 20 or less carbon atoms, an alkoxy group containing 1 or more and 20 or less carbon atoms, an optionally substituted aryl group, an alkyl ester group containing 1 or more and 20 or less carbon atoms, an optionally substituted amino group, or a cyano group, $R_1$ and $R_6$ independently denote a hydrogen atom, a halogen atom, an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group, m is an integer in the range of 1 to 3, and a plurality of $R_3$'s and $R_4$'s may be the same or different.

2. The composition according to claim 1, wherein the compound having an absorption peak at 400 nm or more and 600 nm or less in its colored state has the following general formula [2]:

[Chem. 3]

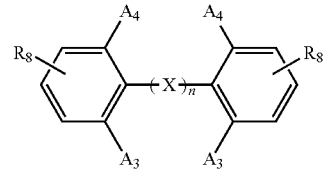

[2]

wherein $A_3$ and $A_4$ independently denote a hydrogen atom, an alkyl group containing 1 or more and 20 or less carbon atoms, an alkoxy group containing 1 or more and 20 or less carbon atoms, or an optionally substituted aryl group, provided that at least one of $A_3$ and $A_4$ denotes the alkyl group, the alkoxy group, or the aryl group, the aryl group may have an alkyl group containing 1 or more and 4 or less carbon atoms or an alkoxy group containing 1 or more and 4 or less carbon atoms as a substituent, $R_8$ denotes a hydrogen atom, a halogen atom, an alkyl group containing 1 or more and 20 or less carbon atoms, an alkoxy group containing 1 or more and 20 or less carbon atoms, an alkyl ester group containing 1 or more and 20 or less carbon atoms, an optionally substituted aryl group, an optionally substituted amino group, or a cyano group, the aryl group may have an alkyl group containing 1 or more and 4 or less carbon atoms as a substituent, X has a structure represented by any of the following general formulae [3] to [6], n is 1 or 2, when n is 2, a plurality of X's are independently selected from the following general formulae [3] to [6]:

[Chem. 4]

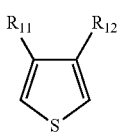

[Chem. 5]

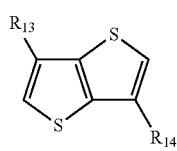

[Chem. 6]

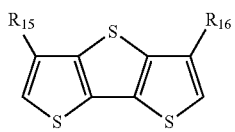

[Chem. 7]

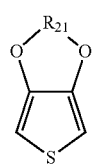

wherein $R_{11}$ to $R_{16}$ independently denote a hydrogen atom, a halogen atom, an alkyl group containing 1 or more and 20 or less carbon atoms, an alkoxy group containing 1 or more and 20 or less carbon atoms, an optionally substituted aryl group, an alkyl ester group containing 1 or more and 20 or less carbon atoms, an optionally substituted amino group, or a cyano group, and $R_{21}$ denotes an optionally branched alkylene group having 1 or more and 20 or less carbon atoms.

3. An electrochromic element, comprising: a pair of electrodes and a electrochromic layer between the pair of electrodes, wherein
the electrochromic layer contains an electrochromic composition and a supporting electrolyte, and
the composition is the organic compound according to claim 1.

4. The electrochromic element according to claim 3, wherein the entire composition shows electrochromic characteristics on one of the pair of electrodes.

5. The electrochromic element according to claim 4, wherein the electrochromic layer further contains another electrochromic compound, and
that other electrochromic compound exhibits electrochromic characteristics on an electrode facing the electrode on which the composition exhibits the electrochromic characteristics.

6. An optical filter, comprising: the electrochromic element according to claim 5; and a TFT element connected to the electrochromic element.

7. A lens unit, comprising: the optical filter according to claim 6; and an imaging optical system.

8. An image pickup apparatus, comprising: the optical filter according to claim 6; an imaging optical system; and an image pickup element configured to take images through the optical filter.

9. The composition according to claim1, wherein m is 2 or 3.

10. An electrochromic elements, comprising: a pair of electrodes and a electrochromic layer between the pair of electrodes, wherein
the electrochromic layer contains an electrochromic composition and a supporting electrolyte, and
the composition is the organic compound according to claim 2.

* * * * *